(12) United States Patent
St. John et al.

(10) Patent No.: US 11,618,914 B2
(45) Date of Patent: Apr. 4, 2023

(54) METHOD FOR THE PRODUCTION OF XYLOBIOSE AND OTHER DEFINED XYLOOLIGOSACCHARIDES

(71) Applicant: The United States of America as Represented by the Secretary of Agriculture, Washington, DC (US)

(72) Inventors: Franz Josef St. John, Madison, WI (US); Merritt Evan Casey Crooks, Madison, WI (US)

(*) Notice: Subject to any disclaimer, the term of this patent is extended or adjusted under 35 U.S.C. 154(b) by 0 days.

(21) Appl. No.: 17/014,024

(22) Filed: Sep. 8, 2020

(65) Prior Publication Data

US 2021/0071218 A1 Mar. 11, 2021

Related U.S. Application Data

(60) Provisional application No. 62/898,077, filed on Sep. 10, 2019.

(51) Int. Cl.
*C12P 19/14* (2006.01)
*C12N 9/24* (2006.01)

(52) U.S. Cl.
CPC ............ *C12P 19/14* (2013.01); *C12N 9/2402* (2013.01); *C12Y 302/01037* (2013.01); *C12Y 302/01055* (2013.01); *C12Y 302/01136* (2013.01); *C12Y 302/01139* (2013.01)

(58) Field of Classification Search
CPC .............. C12N 9/2402; C12N 9/248; C12Y 302/01139; C12Y 302/01055; C12Y 302/01136; C12Y 302/01037; C12P 19/14; C12P 19/12
See application file for complete search history.

(56) References Cited

U.S. PATENT DOCUMENTS 8,338,139 B2 * 12/2012 Lali .................. C12P 19/14 435/96
10,041,136 B2 * 8/2018 St. John ............... C12N 9/2482

OTHER PUBLICATIONS

Devos et al., Practical limits of function prediction. Proteins: Structure, Function, and Genetics. 2000, vol. 41: 98-107. (Year: 2000).*
Izquierdo et al., Complete Genome Sequence of Clostridium clariflavum DSM 19732. Std. Genom. Sci., 2012, vol. 6: 104-115. (Year: 2012).*
Katsimpouras et al., A novel fungal GH30 xylanase with xylobiohydrolase auxiliary activity. Biotechnol. Biofuels., 2019, vol. 12: 120, pp. 1-14. (Year: 2019).*
Kisselev L., Polypeptide release factors in prokaryotes and eukaryotes: same function, different structure. Structure, 2002, vol. 10: 8-9. (Year: 2002).*
Nakamichi et al., Structural and functional characterization of a bifunctional GH30-7 xylanase B from the filamentous fungus *Talaromyces cellulolyticus*. J. Biol. Chem., 2019, vol. 294(11): 4065-4078. (Year: 2019).*
Whisstock et al., Prediction of protein function from protein sequence. Q. Rev. Biophysics., 2003, vol. 36 (3): 307-340. (Year: 2003).*
Wilson et al., Global transcriptome analysis of Clostridium thermocellum ATCC 27405 during growth on dilute acid pretreated Populus and switchgrass Biotechnol. Biofuel., 2013, vol. 6:179, pp. 1-18. (Year: 2013).*
Wishart et al., A single mutation converts a novel phosphotyrosine binding domain into a dual-specificity phosphatase. J. Biol. Chem., 1995, vol. 270(45): 26782-26785. (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Crooks et al., Frontiers Mol. Biosci., 2021, vol. 8, Article 714238, pp. 1-13. (Year: 2021).*
Puchart et al., Biotechnol. Advan., 2021, vol. 47, 107704, pp. 1-16. (Year: 2021).*
Sadowski et al., Current Opinion in Structural Biology 19:357-362, 2009. (Year: 2009).*
Suchova et al., Appl. Microbiol. Biotechnol., 2021, vol. 105: 185-195. (Year: 2021).*
Tang et al. Phil Trans R Soc B 368:20120318, pp. 1-10, 2013. (Year: 2013).*
Urbániková, L., Vršanská, M., Morkeberg Krogh, K.B., Hoff, T., and Biely, P. (2011). Structural basis for substrate recognition by Erwinia chrysanthemi GH30 glucuronoxylanase. FEBS J. 278, 2105.
Vazquez, M., Alonso, J., Dominguez, H., and Parajo, J. (2000). Xylooligosaccharides manufacture and applications. Trends in Food Science & Technology 11(11), 387-393.
Vršanská, M., Kolenová, K., Puchart, V., and Biely, P. (2007). Mode of action of glycoside hydrolase family 5 glucuronoxylan xylanohydrolase from Erwinia chrysanthemi. FEBS J. 274(7), 1666-1677.
Yang, J., Summanen, P.H., Henning, S.M., Hsu, M., Lam, H.M., Huang, J., et al. (2015). Xylooligosaccharide supplementation alters gut bacteria in both healthy and prediabetic adults: a pilot study. Frontiers in physiology 6, 216.
Aachary, A.A., and Prapulla, S.G. (2011). Xylooligosaccharides (XOS) as an emerging prebiotic: microbial synthesis, utilization, structural characterization, bioactive properties, and applications. Comprehensive Reviews in Food Science and Food Safety 10(1), 2-16.
Artzi, L., Morag, E., Barak, Y., Lamed, R., and Bayer, E.A. (2015). Clostridium clariflavum: key cellulosome players are revealed by proteomic analysis. MBio 6(3), e00411-00415.
Bounias, M. (1980). N-(1-Naphthyl) ethylenediamine dihydrochloride as a new reagent for nanomole quantification of sugars on thin-layer plates by a mathematical calibration process. Anal. Biochem. 106(2), 291-295.

(Continued)

*Primary Examiner* — Ganapathirama Raghu

(57) ABSTRACT

The present invention provides compositions, methods, and kits based on a novel two-enzyme system. This system uses a combination of an appendage dependent endoxylanase and xylobiohydrolase activity to produce xylobiose and xylan-derived oligosaccharides using lignocellulosic biomass material, an enriched xylan fraction thereof, or an extracted, purified xylan material as a starting material.

19 Claims, 8 Drawing Sheets
(8 of 8 Drawing Sheet(s) Filed in Color)

Specification includes a Sequence Listing.

(56) References Cited

OTHER PUBLICATIONS

Broekaert, W.F., Courtin, C.M., Verbeke, K., Van de Wiele, T., Verstraete, W., and Delcour, J.A. (2011). Prebiotic and other health-related effects of cereal-derived arabinoxylans, arabinoxylan-oligosaccharides, and xylooligosaccharides. Critical reviews in food science and nutrition 51(2), 178-194.

Charalampopoulos, D., and Rastall, R.A. (2012). Prebiotics in foods. Current opinion in biotechnology 23(2), 187-191.

Chen, H.H., Chen, Y.K., Chang, H.C., and Lin, S.Y. (2012). Immunomodulatory effects of xylooligosaccharides. Food Science and Technology Research 18(2), 195-199.

Chung, Y.-C., Hsu, C.-K., Ko, C.-Y., and Chan, Y.-C. (2007). Dietary intake of xylooligosaccharides improves the intestinal microbiota, fecal moisture, and pH value in the elderly. Nutrition Research 27(12), 756-761.

Crittenden, R.a., and Playne, M.J. (1996). Production, properties and applications of food-grade oligosaccharides. Trends in food science & technology 7(11), 353-361.

Da Silva, A.E., Marcelino, H.R., Gomes, M.C.S., Oliveira, E.E., Nagashima Jr, T., and Egito, E.S.T. (2012). Xylan, a promising hemicellulose for pharmaceutical use.

Daus, S., Petzold-Welcke, K Kötteritzsch, M., Baumgaertel, A., Schubert, U.S., and Heinze, T. (2011). Homogeneous sulfation of xylan from different sources. Macromolecular Materials and Engineering 296(6), 551-561.

Ebringerova, A., and Hromadkova, Z. (1999). Xylans of industrial and biomedical importance. Biotechnology & genetic engineering reviews 16, 325-346.

Ebringerová, A., Kardošová, A., Hromádková, Z., Malovíková, A., and Hříbalová, V. (2002). Immunomodulatory activity of acidic xylans in relation to their structural and molecular properties. International journal of biological macromolecules 30(1), 1-6. QB\64721022.1.

Escalante, A., Gonçalves, A., Bodin, A., Stepan, A., Sandström, C., Toriz, G., et al. (2012). Flexible oxygen barrier films from spruce xylan. Carbohydrate Polymers 87(4), 2381-2387.

Felsenstein J. (1985). Confidence limits on phylogenies: An approach using the bootstrap. Evolution 39:783-791.

Femia, A.P., Salvadori, M., Broekaert, W.F., François, I.E., Delcour, J.A., Courtin, C.M., et al. (2010). Arabinoxylan-oligosaccharides (AXOS) reduce preneoplastic lesions in the colon of rats treated with 1, 2-dimethylhydrazine (DMH). European journal of nutrition 49(2), 127-132.

Finegold, S.M., Li, Z., Summanen, P.H., Downes, J., Thames, G., Corbett, K., et al. (2014). Xylooligosaccharide increases bifidobacteria but not lactobacilli in human gut microbiota. Food & Function 5(3), 436-445.

Gerayiou, Z., Souffreau, C., Rurangwa, E., D'hondt, S., Callewaert, L., Courtin, C.M., et al. (2012). Effects of arabinoxylan-oligosaccharides (AXOS) on juvenile Siberian sturgeon 15 (*Acipenser baerii*) performance, immune responses and gastrointestinal microbial community. Fish & shellfish immunology 33(4), 718-724.

Gibson, G.R., Hutkins, R., Sanders, M.E., Prescott, S.L., Reimer, R.A., Salminen, S.J., et al. (2017). Expert consensus document: The International Scientific Association for Probiotics and Prebiotics (ISAPP) consensus statement on the definition and scope of prebiotics. Nature Reviews Gastroenterology &Amp; Hepatology 14, 491. doi: 10.1038/nrgastro.2017.75.

Gibson, G.R., and Roberfroid, M.B. (1995). Dietary modulation of the human colonic microbiota: introducing the concept of prebiotics. The Journal of nutrition 125(6), 1401-1412.

Goodrich, L.R., and Nixon, A.J. (2006). Medical treatment of osteoarthritis in the horse—a review. The Veterinary Journal 171(1), 51-69.

Hsu, C.-K., Liao, J.-W., Chung, Y.-C., Hsieh, C.-P., and Chan, Y.-C. (2004). Xylooligosaccharides and fructooligosaccharides affect the intestinal microbiota and precancerous colonic lesion development in rats. The Journal of nutrition 134(6), 1523-1528.

Jones D.T., Taylor W.R., and Thornton J.M. (1992). The rapid generation of mutation data matrices from protein sequences. Computer Applications in the Biosciences 8: 275-282.

Kamdem, D.P., Shen, Z., Nabinejad, O., and Shu, Z. (2019). Development of biodegradable composite chitosan-based films incorporated with xylan and carvacrol for food packaging application. Food Packaging and Shelf Life 21, 100344.

Kaprelyants, L., Zhurlova, O., Shpyrko, T., and Pozhitkova, L. (2017). Xylooligosaccharides from agricultural by-products: characterisation, production and physiological effects. Food Science and Technology 11(3).

Kardošová, A., Ebringerová, A., Alföldi, J., Nosál'ová, G., Matáková, T., and Hříbalová, V. (2004). Structural features and biological activity of an acidic polysaccharide complex from Mahonia aquifolium (Pursh) Nutt. Carbohydrate polymers 57(2), 165-176.

Khat-udomkiri, N., Toejing, P., Sirilun, S., Chaiyasut, C., and Lailerd, N. (2020). Antihyperglycemic effect of rice husk derived xylooligosaccharides in high-fat diet and low-dose streptozotocin-induced type 2 diabetic rat model. Food science & nutrition 45 8(1), 428-444.

Kobayashi, Y., Wakasugi, E., Ohbuchi, T., Yokoyama, M., Yasui, R., Kuwahata, M., et al. (2011). Acidic Xylooligosaccharide promotes recovery from iron deficiency anemia by enhancing serum iron level in rats. Biomedical Research 22(4), 417-423.

Kumar S., Stecher G., Li M., Knyaz C., and Tamura K. (2018). MEGA X: Molecular Evolutionary Genetics Analysis across computing platforms. Molecular Biology and Evolution 35:1547-1549.

Kuzmenko, V., Hägg, D., Toriz, G., and Gatenholm, P. (2014). In situ forming spruce xylanbased hydrogel for cell immobilization. Carbohydrate polymers 102, 862-868.

Lim, S.H., Kim, Y., Yun, K.N., Kim, J.Y., Jang, J.-H., Han, M.-J., et al. (2016). Plant-based foods containing cell wall polysaccharides rich in specific active monosaccharides protect against myocardial injury in rat myocardial infarction models. Scientific reports 6, 38728.

Mäkeläinen, H., Forssten, S., Saarinen, M., Stowell, J., Rautonen, N., and Ouwehand, A. (2009). Xylo-oligosaccharides enhance the growth of bifidobacteria and Bifidobacterium lactis in a simulated colon model. Beneficial Microbes 1(1), 81-91.

Mano, M.C.R., Neri-Numa, I.A., da Silva, J.B., Paulino, B.N., Pessoa, M.G., and Pastore, G.M. (2017). Oligosaccharide biotechnology: an approach of prebiotic revolution on the industry. Applied Microbiology and Biotechnology, 1-21.

Mathews, S.L., Pawlak, J., and Grunden, A.M. (2015). Bacterial biodegradation and bioconversion of industrial lignocellulosic streams. Applied Microbiology and Biotechnology, 1-16.

McIlwraith, C.W., Frisbie, D.D., and Kawcak, C.E. (2012). Evaluation of intramuscularly administered sodium pentosan polysulfate for treatment of experimentally induced osteoarthritis in horses. American journal of veterinary research 73(5), 628-633.

Munteanu, S.E., Ilic, M.Z., and Handley, C.J. (2000). Calcium pentosan polysulfate inhibits the catabolism of aggrecan in articular cartilage explant cultures. Arthritis & Rheumatism Official Journal of the American College of Rheumatology 43(10), 2211-2218.

Nishitani, K., and Nevins, D. (1991). Glucuronoxylan xylanohydrolase. A unique xylanase with the requirement for appendant glucuronosyl units. Journal of Biological Chemistry 266(10), 6539-6543.

Oehme, D., Ghosh, P., Shimmon, S., Wu, J., McDonald, C., Troupis, J.M., et al. (2014). Mesenchymal progenitor cells combined with pentosan polysulfate mediating disc regeneration at the time of microdiscectomy: a preliminary study in an ovine model. Journal of Neurosurgery: Spine 20(6), 657-669.

Ohbuchi, T., Sakaino, M., Takahashi, T., Azumi, N., Ishikawa, K., Kawazoe, S., et al. (2010). Oral administration of acidic xylooligosaccharides prevents the development of atopic dermatitis-like skin lesions in NC/Nga mice. Journal of nutritional science and vitaminology 56(1), 54-59.

Rhee, M.S., Wei, L., Sawhney, N., Rice, J.D., St John, F.J., Hurlbert, J.C., et al. (2014). Engineering the xylan utilization system in Bacillus subtilis for production of acidic xylooligosaccharides. Applied and environmental microbiology 80(3), 917-927.

(56) References Cited

OTHER PUBLICATIONS

Saha, B.C. (2003). Hemicellulose bioconversion. J. Ind. Microbiol. Biotechnol. 30(5), 279-291.

Saitou N. and Nei M. (1987). The neighbor-joining method: A new method for reconstructing phylogenetic trees. Molecular Biology and Evolution 4:406-425. Schuchman, E.H., Ge, Y., Lai, A., Borisov, Y., Faillace, M., Eliyahu, E., et al. (2013). Pentosan Polysulfate: A Novel Therapy for the Mucopolysaccharidoses. PLOS One 8(1), e54459.

St John, F.J., Dietrich, D., Crooks, C., Balogun, P., de Serrano, V., Pozharski, E., et al. (2018). A plasmid borne, functionally novel glycoside hydrolase family 30 subfamily 8 endoxylanase from solventogenic Clostridium. Biochemical Journal 475(9), 1533-1551.

St John, F. J., Dietrich, D., Crooks, C., Pozharski, E., Gonzalez, J. M., Bales, E., Smith, K. & Hurlbert, J. C. (2014) A novel member of glycoside hydrolase family 30 subfamily 8 with altered substrate specificity, Acta Crystallogr D Biol Crystallogr. 70, 2950-2958.

St John, F.J., Hurlbert, J.C., Rice, J.D., Preston, J.F., and Pozharski, E. (2011). Ligand bound structures of a glycosyl hydrolase family 30 glucuronoxylan xylanohydrolase. J. Mol. Biol. 407(1), 92-109.

St John, F. J., J. M. González and E. Pozharski (2010). "Consolidation of glycosyl hydrolase family 30: a dual domain 4/7 hydrolase family consisting of two structurally distinct groups." FEBS Lett. 584(21): 4435-4441.

St John, F.J., Rice, J.D., and Preston, J.F. (2006a). Characterization of XynC from *Bacillus subtilis* subsp. subtilis strain 168 and analysis of its role in depolymerization of glucuronoxylan. J. Bacteriol. 188(24), 8617-8626.

St John, F.J., Rice, J.D., and Preston, J.F. (2006b). *Paenibacillus* sp. strain JDR-2 and XynA1: a novel system for methylglucuronoxylan utilization. Applied and environmental microbiology 72(2), 1496-1506.

Studier, F.W. (2005). Protein production by auto-induction in high-density shaking cultures. Protein expression and purification 41(1), 207-234. Ünlü, C.H., Günister, E., and Atici, O. (2009). Synthesis and characterization of NaMt biocomposites with corn cob xylan in aqueous media. Carbohydrate Polymers 76(4), 585-592.

\* cited by examiner

SEQUENCE LISTING

<160> NUMBER OF SEQ ID NOS: 20

<210> SEQ ID NO 1
<211> LENGTH: 534
<212> TYPE: PRT
<213> ORGANISM: Hungateiclostridium clariflavum

<400> SEQUENCE: 1

```
Met Arg Lys Thr Val Ser Leu Thr Thr Val Ala Ala Leu Leu Ile Ser
1               5                   10                  15

Met Leu Ile Leu Val Leu Pro Thr Asn Leu Tyr Ala Ala Ser Thr Val
            20                  25                  30

Thr Val Asp Trp Asp Thr Thr Tyr Gln Thr Ile Asp Gly Phe Gly Val
        35                  40                  45

Ser Glu Ala Phe His Gln Ser Asn Asn Ile Ala Arg Leu Gly Glu Thr
    50                  55                  60

Lys Gln Asn Glu Ile Tyr Asp Leu Leu Phe Ser Thr Thr Asp Gly Ala
65                  70                  75                  80

Gly Phe Ser Ile Phe Arg Ser Ile Leu Gly Asp Gly Gly Thr Trp Gly
                85                  90                  95
```

```
Asn Ala Asp Asp Gly Pro Asn Lys Thr Met Gln Pro Ala Glu Asp Val
            100                 105                 110

Trp Asp Trp Asn Glu Ser Asn Asp Asp Gln Ile Pro Met Ile Arg Ala
        115                 120                 125

Ile Gln Ser Lys Tyr Gly Val Asp Gln Ile Leu Tyr Thr Val Trp Ser
    130                 135                 140

Pro Pro Ala Trp Met Lys Thr Asn Gly Ser Val Val Gly Gly Ser Leu
145                 150                 155                 160

Arg Thr Asp Lys Tyr Gln Ala Tyr Ala Thr Tyr Leu Ala Glu His Ile
                165                 170                 175

Lys Asn Tyr Lys Ser Lys Phe Gly Ile Glu Ile Thr His Ile Gly Ile
            180                 185                 190

Gln Asn Glu Pro Asn Leu Glu Thr Ser Tyr Ser Ser Cys Arg Trp Ser
        195                 200                 205

Pro Glu Glu Leu Arg Ile Phe Met Arg Asp Tyr Leu Val Pro Thr Phe
    210                 215                 220

Asp Lys Glu Asn Ile Thr Ala Lys Val Val Phe Ala Glu Asn Met Ser
225                 230                 235                 240

Phe Asn Glu Gln Tyr Ala Ile Asn Ser Leu Asn Asp Pro Ile Ala Val
                245                 250                 255

Lys Arg Val Asp Ile Val Gly Ala His Asn Tyr Gly Ser Ser Tyr Ile
            260                 265                 270

Pro Phe Thr Thr Thr Lys Ser Lys Gly Lys Gly Ile Trp Met Thr Glu
        275                 280                 285

Val Ser Asp Met Asn Gly Asn Asp Thr Thr Ile Asn Asp Gly Leu Arg
    290                 295                 300

Trp Ala Lys Glu Ile His Asp Phe Met Thr Ile Thr Glu Gly Asn Ala
305                 310                 315                 320

Trp Phe Tyr Trp Trp Gly Ala Cys Phe Lys Thr Tyr Asn Gly Glu Gly
                325                 330                 335

Leu Ile Gln Met Asp Leu Asn Ser Lys Thr Tyr Lys Val Ala Lys Arg
            340                 345                 350

Leu Tyr Thr Ile Gly Gln Phe Ser Arg Phe Ile Arg Pro Gly Trp Gln
        355                 360                 365

Arg Ile Glu Ala Thr Lys Asn Pro Val Ser Asn Val Tyr Val Thr Ala
    370                 375                 380

Tyr Lys Asp Pro Lys Thr Gly Lys Phe Ala Ile Val Ala Ile Asn Asn
385                 390                 395                 400

Gly Trp Ser Lys Gln Ser Ile Thr Tyr Thr Leu Lys Gly Phe Ser Pro
                405                 410                 415

Ala Ser Val Thr Pro Tyr Thr Thr Ser Ser Thr Gln Asn Leu Glu Lys
            420                 425                 430

Gly Ser Asp Ile Thr Val Asn Asn Ser Ser Phe Ser Phe Glu Leu Ala
        435                 440                 445

Pro Asn Ser Ile Thr Thr Phe Val Gly Asp Thr Glu Ser Ala Ser Ile
    450                 455                 460

Ile Tyr Gly Asp Val Asn Gly Asp Gly Val Asn Ser Ile Asp Tyr
465                 470                 475                 480

Gly Tyr Met Lys Trp Tyr Leu Leu Gly Gln Ile Asn Ser Phe Pro Val
                485                 490                 495

Asp Asn Gly Asp Lys Val Ala Asp Leu Asp Gly Asp Gly Arg Ile Thr
            500                 505                 510
```

```
Ser Ile Asp Cys Ala Tyr Met Lys Met Tyr Leu Leu Gly Met Ile Gln
            515                 520                 525

Lys Phe Pro Val Glu Gln
        530

<210> SEQ ID NO 2
<211> LENGTH: 606
<212> TYPE: PRT
<213> ORGANISM: Pseudobacteroides cellulosolvens

<400> SEQUENCE: 2

Met Lys Lys Arg Ile Arg Phe Thr Ser Leu Val Thr Leu Leu Thr Phe
1               5                   10                  15

Leu Leu Val Leu Ala Leu Pro Gln Asn Met Tyr Ala Ala Ser Thr Val
            20                  25                  30

Thr Leu Asp Trp Asp Thr Asn Tyr Gln Asn Ile Asp Gly Phe Gly Val
        35                  40                  45

Ser Glu Ala Phe His Gln Ser Asn Asn Ile Ala Leu Leu Gly Asp Thr
    50                  55                  60

Lys Lys Asn Glu Ile Tyr Asp Leu Leu Phe Ser Thr Thr Lys Gly Ala
65                  70                  75                  80

Gly Phe Ser Ile Phe Arg Ser Ile Leu Gly Asp Gly Thr Trp Gly
                85                  90                  95

Asn Ala Glu Asp Gly Pro Asn Lys Thr Met Gln Pro Ser Glu Thr Thr
            100                 105                 110

Trp Asp Trp Lys Glu Ser Asn Asp Asp Gln Ile Pro Met Tyr Lys Glu
        115                 120                 125

Ile Arg Glu Lys Tyr Gly Ile Asp Lys Leu Leu Tyr Thr Ala Trp Ser
    130                 135                 140

Pro Pro Ala Trp Met Lys Ser Asn Gly Ser Thr Ser Arg Gly Thr Ile
145                 150                 155                 160

Lys Ala Asp Lys Tyr Gln Ala Tyr Ala Thr Tyr Leu Ala Glu His Ile
                165                 170                 175

Lys Asn Tyr Lys Ser Lys Phe Gly Ile Asp Ile Thr His Ile Gly Ile
            180                 185                 190

Ser Asn Glu Pro Asn Leu Glu Thr Asn Tyr Ser Ser Cys Thr Trp Ser
        195                 200                 205

Ser Ser Gln Phe Lys Thr Phe Met Lys Asp Tyr Leu Val Pro Thr Phe
    210                 215                 220

Asp Lys Glu Asn Ile Thr Ala Lys Val Ile Met Gly Glu Pro Met Ala
225                 230                 235                 240

Cys Thr Glu Ser Phe Ala Ile Asp Ser Leu Asn Asp Ala Thr Ala Ser
                245                 250                 255

Lys Arg Thr Asp Ile Val Gly Cys His Asn Tyr Gly Ser Thr Tyr Val
            260                 265                 270

Ala Phe Pro Thr Thr Lys Ser Lys Gly Lys Gly Ile Trp Met Thr Glu
        275                 280                 285

Val Ser Asp Met Asn Gly Asn Asp Ile Thr Ile Asn Asp Gly Leu Lys
    290                 295                 300

Trp Ala Lys Glu Val His Asp Phe Met Thr Ile Thr Gln Gly Asn Ser
305                 310                 315                 320

Trp Ser Tyr Trp Trp Gly Ala Cys Tyr Lys Thr His Asn Gly Glu Gly
                325                 330                 335

Leu Ile Gln Met Asn Met Gly Ala Lys Thr Tyr Thr Val Ala Lys Arg
            340                 345                 350
```

```
Leu Tyr Thr Ile Gly Gln Tyr Ala Arg Phe Ile Arg Pro Glu Trp Gln
            355                 360                 365

Arg Phe Ser Ala Thr Ala Ser Pro Val Ser Gly Val Tyr Val Thr Ala
370                 375                 380

Tyr Lys Asp Pro Ala Thr Gly Glu Phe Ala Val Val Ala Ile Asn Asn
385                 390                 395                 400

Gly Ser Ser Asp Gln Ser Val Ser Phe Asn Leu Lys Gly Phe Thr Ala
                405                 410                 415

Ser Ala Val Thr Pro Tyr Thr Thr Ser Ala Ser Gln Asn Leu Ala Glu
            420                 425                 430

Gly Ser Ser Ile Ala Val Ser Gly Ser Ser Phe Thr Gly Asn Leu Pro
            435                 440                 445

Ala Lys Ser Val Thr Thr Phe Val Gly Ala Lys Pro Thr Lys Lys Val
            450                 455                 460

Ser Gly Tyr Ile Ser Ser Ser Ser Asp Leu Lys Glu Gly Phe Lys
465                 470                 475                 480

Val Glu Ala Glu Gly Thr Ser Thr Leu Thr Asp Asp Lys Gly Tyr Phe
                485                 490                 495

Glu Leu Thr Asn Ile Pro Glu Asn Thr Thr Glu Thr Val Lys Ile
            500                 505                 510

Ser Lys Asp Gly Tyr Leu Ala Arg Glu Ile Lys Asn Val Lys Val Ser
            515                 520                 525

Gly Thr Leu Gly Thr Asn Gly Asn Pro Val Glu Ile Trp Ala Gly Asp
            530                 535                 540

Thr Thr Gln Asp Gly Ala Ile Asn Met Ala Asp Val Leu Gln Ile Ala
545                 550                 555                 560

Lys Phe Phe Asn Ser Thr Ser Gly Ser Thr Lys Tyr Asn Ala Glu Ala
                565                 570                 575

Asp Leu Ser Asn Asp Gly Val Val Asn Met Ala Asp Val Leu Ile Val
            580                 585                 590

Ala Lys His Phe Asn Ala Thr Ile Asp Ser Tyr Pro Ala Leu
            595                 600                 605

<210> SEQ ID NO 3
<211> LENGTH: 533
<212> TYPE: PRT
<213> ORGANISM: Ruminiclostridium cellobioparum

<400> SEQUENCE: 3

Met Lys Lys Phe Ile Arg Phe Thr Gly Met Ala Ile Val Leu Met Leu
1               5                   10                  15

Leu Leu Ser Ile Ala Leu Pro Ala Asn Met Tyr Ala Ala Ser Ala Val
            20                  25                  30

Thr Val Asp Trp Asn Thr Ala Tyr Gln Thr Ile Asp Gly Phe Gly Val
            35                  40                  45

Ser Glu Ala Phe His Gln Ser Asn Asn Ile Ala Leu Leu Gly Glu Ala
    50                  55                  60

Lys Gln Asn Glu Ile Tyr Asp Leu Leu Phe Ser Thr Asn Gly Ala
65                  70                  75                  80

Gly Phe Ser Ile Phe Arg Ser Ile Leu Gly Asp Gly Thr Trp Gly
                85                  90                  95

Asn Ala Thr Asp Gly Pro Asn Arg Thr Met Gln Pro Ser Glu Thr Thr
            100                 105                 110
```

```
Trp Asp Trp Thr Ala Ser Asn Asp Asp Gln Ile Pro Met Ile Lys Ala
            115                 120                 125

Ile Gln Ser Thr Tyr Gly Ile Lys Asn Ile Leu Tyr Thr Val Trp Ser
        130                 135                 140

Pro Pro Ala Trp Met Lys Thr Gly Ser Val Ala Arg Gly Ser Leu
145                 150                 155                 160

Lys Thr Asp Lys Tyr Gln Ala Tyr Ala Thr Tyr Leu Ala Glu His Ile
                165                 170                 175

Lys Asn Tyr Lys Ser Lys Phe Gly Ile Asp Ile Thr His Ile Gly Ile
            180                 185                 190

Ser Asn Glu Pro Asp Leu Glu Thr Ala Tyr Ser Ser Cys Thr Trp Thr
        195                 200                 205

Ala Ala Gln Phe Lys Thr Phe Met Ser Asn Tyr Leu Val Pro Thr Phe
    210                 215                 220

Asp Arg Glu Gly Ile Thr Ala Lys Val Ile Val Gly Glu Lys Met Thr
225                 230                 235                 240

Cys Ser Glu Ser Leu Ala Ile Asp Ser Leu Asn Asp Ala Val Ala Val
                245                 250                 255

Lys Arg Thr Asp Ile Val Gly Cys His Asn Tyr Gly Ser Thr Tyr Val
            260                 265                 270

Pro Phe Pro Thr Thr Lys Ala Lys Gly Lys Gly Ile Trp Gln Thr Glu
        275                 280                 285

Ile Ser Asp Met Asn Gly Asn Asp Ile Thr Ile Thr Asp Gly Leu Lys
    290                 295                 300

Trp Ser Arg Glu Ile His Asp Phe Met Thr Val Thr Gln Gly Asn Ala
305                 310                 315                 320

Trp Asn Tyr Trp Trp Gly Ala Cys Tyr Lys Thr Tyr Asn Gly Glu Gly
                325                 330                 335

Leu Ile Gln Met Asp Met Asn Ser Lys Thr Tyr Lys Val Ala Lys Arg
            340                 345                 350

Leu Tyr Thr Ile Gly Gln Tyr Ala Arg Phe Ile Arg Pro Gly Trp Gln
        355                 360                 365

Arg Ile Ser Ala Thr Ala Asn Pro Val Ser Gly Ile Tyr Val Thr Ala
    370                 375                 380

Tyr Lys Asp Pro Ser Thr Gly Asn Phe Ala Ile Val Ala Met Asn Asn
385                 390                 395                 400

Ser Ser Ala Gly Gln Ser Val Thr Tyr Thr Leu Asn Gly Phe Ser Pro
                405                 410                 415

Ser Ser Val Thr Pro Phe Thr Thr Ser Ala Thr Gln Asn Leu Ala Glu
            420                 425                 430

Gly Ala Lys Ile Ala Val Ser Gly Ser Ser Phe Thr Gly Thr Ile Ala
        435                 440                 445

Ala Asn Ser Ile Thr Thr Phe Val Gly Ser Thr Gly Ser Ser Gln Glu
    450                 455                 460

Ile Tyr Gly Asp Val Asn Gly Asp Arg Val Val Asp Ala Leu Asp Phe
465                 470                 475                 480

Ala Leu Val Lys Gln Tyr Leu Thr Gly Gln Ile Ser Thr Phe Pro Ser
                485                 490                 495

Gln Asp Gly Ile Arg Leu Ala Asp Val Asn Arg Asp Ser Ser Val Asp
            500                 505                 510

Ala Leu Asp Leu Ala Ile Leu Lys Lys Tyr Leu Leu Gly Glu Ile Ile
        515                 520                 525
```

Thr Leu Pro Val Asn
    530

<210> SEQ ID NO 4
<211> LENGTH: 531
<212> TYPE: PRT
<213> ORGANISM: Ruminiclostridium hungatei

<400> SEQUENCE: 4

Met Lys Arg Phe Asn Arg Leu Thr Cys Ile Ala Ile Ala Leu Met Ile
1               5                   10                  15

Leu Leu Ser Leu Ala Leu Pro Gln Gln Leu Phe Ala Ala Ser Thr Val
            20                  25                  30

Thr Val Gly Trp Asn Thr Val Tyr Gln Ser Ile Asp Gly Phe Gly Val
        35                  40                  45

Ser Glu Ala Phe His Gln Ser Asn Asn Ile Ala Leu Leu Gly Glu Thr
    50                  55                  60

Lys Gln Lys Glu Ile Tyr Asp Leu Leu Phe Ser Thr Thr Gln Gly Ala
65                  70                  75                  80

Gly Phe Ser Ile Phe Arg Ser Ile Leu Gly Asp Gly Thr Trp Gly
                85                  90                  95

Asn Ala Thr Asp Gly Pro Asn Lys Thr Met Gln Pro Ser Glu Thr Thr
            100                 105                 110

Trp Asp Trp Ser Glu Ser Asn Asp Asp Gln Ile Pro Met Ile Arg Ala
        115                 120                 125

Ile Gln Ala Ala Tyr Gly Ile Lys Asn Ile Gln Tyr Ser Val Trp Ser
130                 135                 140

Pro Pro Ala Trp Met Lys Thr Asn Gly Ser Val Ala Gly Gly Ser Val
145                 150                 155                 160

Lys Ala Asp Lys Tyr Gln Ala Tyr Ala Thr Tyr Leu Ala Glu His Ile
                165                 170                 175

Lys Asn Tyr Lys Ser Lys Phe Gly Ile Glu Ile Thr His Ile Gly Ile
            180                 185                 190

Ser Asn Glu Pro Asp Leu Thr Thr Ala Tyr Ser Ser Cys Thr Trp Thr
        195                 200                 205

Gly Ala Gln Phe Lys Ala Phe Met Lys Asp Ala Leu Val Pro Thr Phe
210                 215                 220

Asp Arg Glu Gly Ile Thr Ala Lys Val Ile Met Gly Glu Lys Met Thr
225                 230                 235                 240

Cys Ser Glu Ser Leu Ala Ile Asp Cys Leu Asn Asp Ala Val Ala Val
                245                 250                 255

Thr Arg Thr Asp Ile Val Gly Cys His Asn Tyr Gly Ser Ser Tyr Ala
            260                 265                 270

Thr Phe Pro Thr Thr Lys Ala Lys Gly Lys Gly Ile Trp Gln Thr Glu
        275                 280                 285

Ile Ser Asp Met Asn Gly Asn Asp Ile Thr Ile Thr Asp Gly Leu Lys
290                 295                 300

Trp Ser Lys Gln Ile Tyr Asp Phe Met Thr Ile Thr Gln Gly Asn Ala
305                 310                 315                 320

Trp Asn Tyr Trp Trp Gly Ala Cys Tyr Lys Thr Tyr Asn Gly Glu Gly
                325                 330                 335

Leu Ile Gln Met Asp Met Asn Ala Lys Thr Tyr Lys Val Ala Lys Arg
            340                 345                 350

Leu Tyr Thr Ile Gly Gln Tyr Ser Arg Phe Ile Arg Pro Gly Trp Gln
        355                 360                 365

```
Arg Ile Ser Ala Thr Ala Asn Pro Val Ser Gly Val Tyr Val Thr Ala
        370                 375                 380

Tyr Lys Asp Pro Ala Thr Gly Lys Phe Ala Ile Val Ala Met Asn Asp
385                 390                 395                 400

Ser Ser Thr Asn Gln Ser Leu Thr Tyr Thr Leu Asp Gly Phe Ser Pro
                405                 410                 415

Ala Ser Val Thr Pro Tyr Thr Thr Ser Ala Thr Gln Asn Leu Ala Glu
                420                 425                 430

Gly Ser Lys Ile Ala Val Ser Gly Ser Ser Phe Thr Ala Ser Leu Ala
                435                 440                 445

Gly Asn Ser Ile Thr Thr Phe Val Gly Glu Ile Asn Ala Gly Leu Tyr
                450                 455                 460

Gly Asp Val Asn Asp Asp Lys Ala Val Asp Ala Ile Asp Phe Ala Leu
465                 470                 475                 480

Val Lys Gln Tyr Leu Thr Arg Gln Ile Ser Thr Phe Pro Ser Lys Asp
                485                 490                 495

Gly Leu Arg Leu Ala Asp Val Asn Ile Asp Gly Ser Val Asp Ala Ile
                500                 505                 510

Asp Leu Ala Met Leu Lys Lys Tyr Leu Leu Gly Asp Ile Lys Thr Leu
                515                 520                 525

Pro Val Asn
    530

<210> SEQ ID NO 5
<211> LENGTH: 532
<212> TYPE: PRT
<213> ORGANISM: Ruminiclostridium papyrosolvens

<400> SEQUENCE: 5

Met Ile Lys Met Ile Arg Leu Leu Ser Leu Thr Met Val Leu Met Leu
1               5                   10                  15

Leu Leu Thr Met Ala Met Pro Leu Asn Leu Tyr Ala Ala Ser Thr Val
                20                  25                  30

Thr Val Asp Trp Asp Thr Asn Tyr Gln Ala Ile Asp Gly Phe Gly Val
                35                  40                  45

Ser Glu Ala Phe His Gln Ser Asn Asn Ile Ala Leu Leu Gly Asp Thr
            50                  55                  60

Lys Lys Lys Glu Ile Tyr Asp Leu Leu Phe Ser Thr Ser Lys Gly Ala
65              70                  75                  80

Gly Phe Ser Ile Phe Arg Ser Ile Leu Gly Asp Gly Thr Trp Gly
                85                  90                  95

Asn Ala Thr Asp Gly Pro Asn Lys Thr Met Gln Pro Ser Glu Thr Thr
                100                 105                 110

Trp Asp Trp Lys Glu Thr Asn Asp Asp Gln Ile Ser Ile Ile Arg Glu
                115                 120                 125

Ile Gln Ser Ala Tyr Gly Ile Asn Lys Ile Leu Tyr Thr Val Trp Ser
            130                 135                 140

Pro Pro Ala Trp Met Lys Ser Asn Gly Ser Thr Ser Arg Gly Tyr Leu
145                 150                 155                 160

Lys Thr Asp Lys Tyr Gln Ala Tyr Ala Thr Tyr Leu Ala Glu His Ile
                165                 170                 175

Lys Asn Tyr Lys Ser Lys Phe Gly Ile Asp Ile Thr His Ile Gly Ile
                180                 185                 190
```

Ser Asn Glu Pro Asn Leu Glu Thr Asp Tyr Ser Ser Cys Thr Trp Thr
            195                 200                 205

Ser Ala Gln Phe Lys Thr Phe Met Lys Asp Tyr Leu Val Pro Thr Phe
    210                 215                 220

Asp Lys Glu Gly Ile Thr Ala Lys Val Ile Met Gly Glu Pro Met Ser
225                 230                 235                 240

Cys Thr Glu Ser Phe Ala Ile Asp Ser Leu Asn Asp Ala Thr Ala Leu
                245                 250                 255

Thr Arg Thr Asp Ile Val Gly Cys His Asn Tyr Gly Ser Ser Tyr Thr
                    260                 265                 270

Thr Phe Pro Thr Thr Lys Ala Lys Gly Lys Gly Ile Trp Gln Thr Glu
                275                 280                 285

Ile Ser Asp Met Asn Gly Asn Asp Ile Thr Ile Thr Asp Gly Leu Lys
            290                 295                 300

Trp Ser Lys Gln Ile Phe Asp Phe Met Thr Ile Thr Gln Gly Asn Ala
305                 310                 315                 320

Trp Asn Tyr Trp Trp Gly Ala Cys Tyr Lys Thr Tyr Asn Gly Glu Gly
                325                 330                 335

Leu Ile Gln Met Asp Met Asn Ser Lys Thr Tyr Lys Ile Ala Lys Arg
                340                 345                 350

Leu Tyr Thr Ile Gly Gln Tyr Ser Arg Phe Ile Arg Pro Gly Trp Gln
            355                 360                 365

Arg Phe Ser Ala Thr Ser Asn Pro Val Ser Asn Val Tyr Val Thr Ala
            370                 375                 380

Tyr Lys Asp Pro Ala Thr Gly Lys Phe Ala Ile Val Ala Met Asn Asp
385                 390                 395                 400

Gly Ser Thr Asn Gln Ser Ile Thr Tyr Thr Leu Lys Gly Phe Thr Pro
                405                 410                 415

Asp Ser Val Thr Pro Tyr Thr Thr Ser Ser Thr Gln Asp Leu Ala Glu
                420                 425                 430

Gly Thr Lys Ile Thr Val Ser Gly Gly Ser Phe Thr Ala Thr Leu Ala
            435                 440                 445

Ala Asn Ser Ile Thr Thr Phe Val Gly Gly Asp Val Asn Pro Gly
            450                 455                 460

Ile Tyr Gly Asp Val Asn Gly Asp Lys Val Val Asp Ala Ile Asp Phe
465                 470                 475                 480

Ala Leu Tyr Lys Gln Tyr Leu Ile Lys Gln Ile Ser Thr Phe Pro Ser
                485                 490                 495

Pro Asp Gly Met Lys Leu Ala Ser Val Asn Gly Asp Asn Ser Val Asp
                500                 505                 510

Ala Ile Asp Phe Ala Leu Val Lys Lys Tyr Leu Leu Gly Ser Ile Pro
            515                 520                 525

Lys Leu Pro Val
        530

<210> SEQ ID NO 6
<211> LENGTH: 532
<212> TYPE: PRT
<213> ORGANISM: Ruminiclostridium cellulolyticum

<400> SEQUENCE: 6

Met Lys Lys Ile Ile Arg Leu Leu Gly Leu Thr Met Val Leu Met Leu
1               5                   10                  15

```
Val Phe Thr Met Val Leu Pro Leu Asn Leu Tyr Ala Ala Ser Thr Val
             20                  25                  30

Thr Val Asp Trp Gly Thr Asn Tyr Gln Thr Ile Asp Gly Phe Gly Val
         35                  40                  45

Ser Glu Ala Phe His Gln Ser Asn Asn Ile Ala Leu Leu Gly Asp Thr
 50                  55                  60

Lys Lys Lys Glu Ile Tyr Asp Leu Leu Phe Ser Thr Thr Lys Gly Ala
 65                  70                  75                  80

Gly Phe Ser Ile Phe Arg Ser Ile Leu Gly Asp Gly Thr Trp Gly
                 85                  90                  95

Asn Ala Thr Asp Gly Pro Asn Lys Thr Met Gln Pro Ser Glu Thr Thr
             100                 105                 110

Trp Asp Trp Lys Glu Ser Asn Asp Asp Gln Ile Ser Met Ile Arg Glu
         115                 120                 125

Ile Gln Ser Gly Tyr Gly Ile Asn Lys Ile Leu Tyr Thr Val Trp Ser
 130                 135                 140

Pro Pro Ala Trp Met Lys Ser Asn Gly Ser Thr Ser Arg Gly Tyr Leu
145                 150                 155                 160

Lys Thr Asp Lys Tyr Gln Ala Tyr Ala Thr Tyr Leu Ala Glu His Ile
                 165                 170                 175

Lys Asn Tyr Lys Ser Lys Phe Gly Ile Asp Ile Thr His Ile Gly Ile
             180                 185                 190

Ser Asn Glu Pro Asn Leu Glu Thr Asp Tyr Ser Ser Cys Thr Trp Thr
         195                 200                 205

Ala Ala Gln Phe Lys Thr Phe Met Lys Asp Tyr Leu Val Pro Thr Phe
 210                 215                 220

Asp Lys Glu Gly Ile Thr Ala Lys Val Ile Met Gly Glu Pro Met Ser
225                 230                 235                 240

Cys Thr Glu Ser Phe Ala Ile Asp Cys Leu Asn Asp Ala Thr Ala Leu
                 245                 250                 255

Thr Arg Thr Asp Ile Val Gly Cys His Asn Tyr Gly Ser Ser Tyr Thr
             260                 265                 270

Thr Phe Pro Thr Thr Lys Ala Lys Gly Lys Gly Ile Trp Gln Thr Glu
         275                 280                 285

Ile Ser Asp Met Asn Gly Asn Asp Thr Thr Ile Thr Asp Gly Leu Lys
 290                 295                 300

Trp Ser Lys Gln Ile Phe Asp Phe Met Thr Ile Thr Gln Gly Asn Ala
305                 310                 315                 320

Trp Asn Tyr Trp Trp Gly Ala Cys Tyr Lys Thr Tyr Asn Gly Glu Gly
                 325                 330                 335

Leu Ile Gln Met Asp Met Asn Ser Lys Thr Tyr Lys Val Ala Lys Arg
             340                 345                 350

Leu Tyr Thr Val Gly Gln Tyr Ser Arg Phe Ile Arg Pro Gly Trp Gln
         355                 360                 365

Arg Phe Ala Ala Thr Ser Asn Pro Val Ser Asn Val Tyr Val Thr Ala
 370                 375                 380

Tyr Lys Asp Pro Ala Thr Gly Lys Phe Ala Ile Val Ala Met Asn Asp
385                 390                 395                 400

Gly Tyr Thr Asn Gln Ser Ile Thr Tyr Thr Leu Lys Gly Phe Thr Pro
                 405                 410                 415

Asp Ser Val Thr Pro Tyr Thr Thr Ser Ser Thr Gln Asp Leu Ala Glu
             420                 425                 430
```

```
Gly Thr Lys Ile Thr Val Ser Gly Ser Phe Thr Ala Asn Leu Ala
            435                 440                 445

Ala Asn Ser Ile Thr Thr Phe Val Gly Ser Asp Val Asn Pro Gly
    450                 455                 460

Ile Tyr Gly Asp Val Asn Gly Asp Lys Val Val Asp Ala Ile Asp Phe
465                 470                 475                 480

Ala Leu Tyr Lys Gln Tyr Leu Ile Lys Gln Ile Ser Thr Phe Pro Ser
                485                 490                 495

Pro Asp Gly Met Lys Leu Ala Asp Val Asn Gly Asp Asn Ser Val Asp
                500                 505                 510

Ala Ile Asp Phe Ala Leu Ile Lys Lys Tyr Leu Leu Gly Ser Ile Thr
            515                 520                 525

Lys Leu Pro Val
        530

<210> SEQ ID NO 7
<211> LENGTH: 532
<212> TYPE: PRT
<213> ORGANISM: Clostridium sp.

<400> SEQUENCE: 7

Met Lys Lys Met Ile Arg Leu Leu Ser Leu Ser Met Val Leu Met Leu
1               5                   10                  15

Val Phe Thr Met Ala Leu Pro Leu Asn Leu Tyr Ala Ala Ser Thr Val
            20                  25                  30

Thr Val Asp Trp Asp Thr Asn Tyr Gln Ala Ile Asp Gly Phe Gly Val
        35                  40                  45

Ser Glu Ala Phe His Gln Ser Asn Asn Ile Ala Leu Leu Gly Asp Thr
50                  55                  60

Lys Lys Lys Glu Ile Tyr Asp Leu Leu Phe Ser Thr Ser Lys Gly Ala
65                  70                  75                  80

Gly Phe Ser Ile Phe Arg Ser Ile Leu Gly Asp Gly Gly Thr Trp Gly
                85                  90                  95

Asn Ala Thr Asp Gly Pro Asn Lys Thr Met Gln Pro Ser Glu Thr Thr
            100                 105                 110

Trp Asp Trp Lys Glu Thr Asn Asp Asp Gln Ile Ser Met Ile Arg Glu
        115                 120                 125

Ile Lys Ser Ala Tyr Gly Ile Asp Lys Ile Leu Tyr Thr Val Trp Ser
130                 135                 140

Pro Pro Ala Trp Met Lys Ser Asn Gly Ser Thr Ser Arg Gly Tyr Leu
145                 150                 155                 160

Lys Thr Asp Lys Tyr Gln Ala Tyr Ala Thr Tyr Leu Ala Glu His Ile
                165                 170                 175

Lys Asn Tyr Lys Ser Lys Phe Gly Ile Asp Ile Thr His Ile Gly Ile
            180                 185                 190

Ser Asn Glu Pro Asn Leu Glu Thr Asp Tyr Ser Ser Cys Thr Trp Thr
        195                 200                 205

Ser Ala Gln Phe Lys Thr Phe Met Lys Asp Tyr Leu Val Pro Thr Phe
210                 215                 220

Asp Lys Glu Gly Ile Thr Ala Lys Val Ile Met Gly Glu Pro Met Ser
225                 230                 235                 240

Cys Thr Glu Ser Phe Ala Ile Asp Ser Leu Asn Asp Ala Thr Ala Leu
                245                 250                 255

Thr Arg Thr Asp Ile Val Gly Cys His Asn Tyr Gly Ser Ser Tyr Thr
            260                 265                 270
```

```
Thr Phe Pro Thr Thr Lys Ala Lys Gly Lys Gly Ile Trp Gln Thr Glu
            275                 280                 285

Ile Ser Asp Met Asn Gly Asn Asp Ile Thr Ile Thr Asp Gly Leu Lys
        290                 295                 300

Trp Ser Lys Gln Ile Phe Asp Phe Met Thr Ile Thr Gln Gly Asn Ala
305                 310                 315                 320

Trp Asn Tyr Trp Trp Gly Ala Cys Tyr Lys Thr Tyr Asn Gly Glu Gly
                325                 330                 335

Leu Ile Gln Met Asp Met Asn Ser Lys Thr Tyr Lys Ile Ala Lys Arg
            340                 345                 350

Leu Tyr Thr Ile Gly Gln Tyr Ser Arg Phe Ile Arg Pro Gly Trp Gln
            355                 360                 365

Arg Phe Ser Ala Thr Ser Asn Pro Val Ser Asn Val Tyr Val Thr Ala
        370                 375                 380

Tyr Lys Asp Pro Ala Thr Gly Lys Phe Ala Ile Val Ala Met Asn Asp
385                 390                 395                 400

Gly Ser Thr Asn Gln Ser Ile Thr Tyr Thr Leu Lys Gly Phe Thr Pro
                405                 410                 415

Asp Ser Val Thr Pro Tyr Thr Thr Ser Ser Thr Gln Asp Leu Ala Glu
            420                 425                 430

Gly Thr Lys Ile Thr Val Asn Gly Gly Ser Phe Thr Ala Asn Leu Ala
            435                 440                 445

Ala Asn Ser Ile Thr Thr Phe Val Gly Gly Gly Asp Val Asn Pro Gly
        450                 455                 460

Ile Tyr Gly Asp Val Asn Gly Asp Lys Val Val Asp Ala Ile Asp Phe
465                 470                 475                 480

Ala Leu Phe Lys Gln Tyr Leu Ile Lys Gln Ile Ser Thr Phe Pro Ser
                485                 490                 495

Pro Asp Gly Met Lys Phe Ala Asp Val Asn Gly Asp Asn Ser Val Asp
            500                 505                 510

Ala Ile Asp Phe Ala Leu Ile Lys Lys Tyr Leu Leu Gly Ser Ile Pro
            515                 520                 525

Lys Leu Pro Val
        530

<210> SEQ ID NO 8
<211> LENGTH: 532
<212> TYPE: PRT
<213> ORGANISM: Ruminiclostridium papyrosolvens

<400> SEQUENCE: 8

Met Lys Lys Ile Ile Arg Leu Leu Gly Leu Thr Met Val Leu Met Leu
1               5                   10                  15

Val Phe Thr Met Val Leu Pro Leu Asn Leu Tyr Ala Ala Ser Thr Val
            20                  25                  30

Thr Val Asp Trp Asn Thr Asn Tyr Gln Gly Ile Asp Gly Phe Gly Val
        35                  40                  45

Ser Glu Ala Phe His Gln Ser Asn Asn Ile Ala Leu Leu Gly Asp Ser
    50                  55                  60

Lys Lys Lys Glu Ile Tyr Asp Leu Leu Phe Ser Thr Ser Lys Gly Ala
65                  70                  75                  80

Gly Phe Ser Ile Phe Arg Ser Ile Leu Gly Asp Gly Thr Trp Gly
                85                  90                  95
```

```
Asn Ala Thr Asp Gly Pro Asn Lys Thr Met Gln Pro Ser Glu Thr Thr
            100                 105                 110

Trp Asp Trp Lys Glu Ser Asn Asp Gln Ile Ser Met Ile Arg Glu
            115                 120                 125

Ile Gln Ser Gly Tyr Gly Ile Asn Lys Ile Leu Tyr Thr Val Trp Ser
            130                 135                 140

Pro Pro Ala Trp Met Lys Ser Asn Gly Ser Thr Ser Arg Gly Tyr Leu
145                 150                 155                 160

Lys Thr Asp Lys Tyr Gln Ala Tyr Ala Thr Tyr Leu Ala Glu His Ile
                165                 170                 175

Lys Asn Tyr Lys Ser Lys Phe Gly Ile Asp Ile Thr His Ile Gly Ile
            180                 185                 190

Ser Asn Glu Pro Asn Leu Glu Thr Asp Tyr Ser Ser Cys Thr Trp Thr
            195                 200                 205

Ser Ala Gln Phe Lys Thr Phe Met Lys Asp Tyr Leu Val Pro Thr Phe
210                 215                 220

Asp Lys Glu Gly Ile Thr Ala Lys Val Ile Met Gly Glu Pro Met Ser
225                 230                 235                 240

Cys Thr Glu Ser Phe Ala Ile Asp Ser Leu Asn Asp Ser Thr Ala Val
                245                 250                 255

Thr Arg Thr Asp Ile Val Gly Cys His Asn Tyr Gly Ser Ser Tyr Thr
                260                 265                 270

Thr Phe Pro Thr Thr Lys Ala Lys Gly Lys Gly Ile Trp Gln Thr Glu
            275                 280                 285

Ile Ser Asp Met Asn Gly Asn Asp Ile Thr Ile Asn Asp Gly Leu Lys
            290                 295                 300

Trp Ser Lys Gln Ile Phe Asp Phe Met Thr Ile Thr Gln Gly Asn Ala
305                 310                 315                 320

Trp Asn Tyr Trp Trp Gly Ala Cys Tyr Lys Thr Tyr Asn Gly Glu Gly
                325                 330                 335

Leu Ile Gln Leu Asp Met Asn Ser Arg Thr Tyr Lys Ile Ala Lys Arg
            340                 345                 350

Leu Tyr Thr Ile Gly Gln Tyr Ser Arg Phe Ile Arg Pro Gly Trp Gln
            355                 360                 365

Arg Phe Ser Ala Thr Ser Asn Pro Val Ser Asn Val Tyr Val Thr Ala
            370                 375                 380

Tyr Lys Asp Thr Ala Thr Gly Lys Phe Ala Ile Val Ala Met Asn Asp
385                 390                 395                 400

Gly Ser Ser Asn Gln Ser Ile Thr Tyr Thr Leu Lys Gly Phe Thr Pro
                405                 410                 415

Asp Ser Val Thr Pro Tyr Thr Thr Ser Ser Thr Gln Asp Leu Ala Glu
                420                 425                 430

Gly Ser Lys Ile Thr Val Asn Gly Gly Ser Phe Thr Ala Thr Leu Ala
            435                 440                 445

Ala Asn Ser Ile Thr Thr Phe Ala Gly Gly Asp Asn Met Asn Pro Ala
            450                 455                 460

Ile Tyr Gly Asp Val Asn Gly Asp Lys Val Val Asp Ala Ile Asp Ile
465                 470                 475                 480

Val Leu Phe Lys Gln Tyr Leu Ile Asn Gln Ile Ser Thr Phe Pro Ser
                485                 490                 495

Pro Asp Gly Met Lys Leu Ala Asp Val Asn Gly Asp Ser Ser Val Asp
            500                 505                 510
```

```
Ala Ile Asp Phe Ala Leu Ile Lys Lys Tyr Leu Leu Gly Leu Ile Pro
        515                 520                 525

Lys Leu Pro Val
        530

<210> SEQ ID NO 9
<211> LENGTH: 530
<212> TYPE: PRT
<213> ORGANISM: Ruminiclostridium sufflavum

<400> SEQUENCE: 9

Met Lys Arg Met Thr Arg Phe Thr Cys Leu Ala Ile Val Thr Met Leu
1               5                   10                  15

Leu Val Thr Met Leu Ala Pro Ser Ala Ser Tyr Ala Ala Ser Ser Val
            20                  25                  30

Thr Leu Asp Trp Asp Thr Glu Tyr Gln Thr Ile Asp Gly Phe Gly Val
        35                  40                  45

Ser Glu Ala Phe His Gln Ser Asn Asn Ile Ala Leu Leu Gly Thr Ala
    50                  55                  60

Lys Gln Lys Glu Ile Tyr Asp Leu Leu Phe Ser Thr Glu Lys Gly Ala
65                  70                  75                  80

Gly Phe Ser Ile Phe Arg Ser Ile Leu Gly Asp Gly Thr Trp Gly
                85                  90                  95

Asp Ala Gln Asp Gly Pro Asn Lys Thr Met Gln Pro Ser Ala Ser Thr
            100                 105                 110

Trp Asp Trp Lys Glu Ser Asn Asp Gln Ile Pro Met Ile Lys Thr
        115                 120                 125

Ile Gln Ala Asp Tyr Gly Ile Asp Lys Ile Gln Tyr Thr Val Trp Ser
    130                 135                 140

Pro Pro Ala Trp Met Lys Thr Thr Gly Ser Val Ala Gly Gly Ser Leu
145                 150                 155                 160

Ser Thr Asp Lys Tyr Gln Ala Tyr Ala Thr Tyr Leu Ala Glu His Ile
                165                 170                 175

Lys Asn Tyr Lys Ala Lys Phe Gly Ile Glu Ile Thr His Ile Gly Ile
            180                 185                 190

Gln Asn Glu Pro Asp Leu Thr Thr Ala Tyr Ser Ser Cys Val Trp Thr
        195                 200                 205

Ala Ala Gln Phe Lys Thr Phe Met Lys Asp Tyr Leu Val Pro Thr Phe
    210                 215                 220

Asp Lys Glu Gly Ile Thr Ala Lys Val Ile Met Gly Glu Lys Met Thr
225                 230                 235                 240

Cys Ser Glu Ala Met Ala Ile Asp Cys Leu Asn Asp Ala Ala Ala Leu
                245                 250                 255

Thr Arg Thr Asp Ile Val Gly Cys His Asn Tyr Gly Ser Ser Tyr Ala
            260                 265                 270

Ala Phe Pro Thr Thr Lys Ala Lys Gly Lys Gly Ile Trp Gln Thr Glu
        275                 280                 285

Ile Ser Asp Met Asn Gly Asn Asp Leu Thr Ile Thr Asp Gly Leu Asn
    290                 295                 300

Trp Ala Lys Gln Val Tyr Asp Phe Met Thr Val Thr Gln Gly Asn Ala
305                 310                 315                 320

Trp Asn Tyr Trp Trp Gly Ala Cys Tyr Lys Thr Trp Asn Gly Glu Gly
                325                 330                 335

Leu Ile Gln Met Asp Met Asn Ala Lys Thr Tyr Lys Ile Ala Lys Arg
            340                 345                 350
```

```
Leu Tyr Thr Ile Gly Gln Tyr Ala Arg Phe Ile Arg Pro Asp Trp Lys
            355                 360                 365

Arg Phe Glu Ala Thr Lys Asn Pro Val Ser Gly Val Tyr Val Thr Ala
    370                 375                 380

Tyr Lys Asp Pro Glu Thr Gly Lys Phe Ala Val Val Ala Ile Asn Asn
385                 390                 395                 400

Gly Ser Ser Gln Ala Val Thr Tyr Asn Leu Lys Gly Phe Glu Ala
                405                 410                 415

Ala Ser Val Thr Pro Tyr Thr Thr Ser Ala Thr Gln Asn Leu Ala Glu
            420                 425                 430

Gly Ser Glu Ile Ala Leu Asn Gly Thr Ser Phe Ser Ala Thr Leu Ala
            435                 440                 445

Ala Asn Ser Val Thr Thr Phe Val Gly Gly Thr Asp Ser Gly Thr Tyr
            450                 455                 460

Gly Asp Val Asn Gly Asp Asn Ala Val Asp Ala Leu Asp Phe Ala Ile
465                 470                 475                 480

Ile Lys Gln Tyr Leu Ile Gly Gln Ile Ser Thr Phe Pro Gly Lys Asp
                485                 490                 495

Gly Met Lys Leu Ala Asp Val Asn Gln Asp Gly Ser Val Asp Ala Leu
            500                 505                 510

Asp Phe Ala Ile Val Lys Lys Tyr Leu Leu Gly Asn Ile Asp Arg Leu
            515                 520                 525

Pro Val
    530

<210> SEQ ID NO 10
<211> LENGTH: 530
<212> TYPE: PRT
<213> ORGANISM: Ruminiclostridium sp.

<400> SEQUENCE: 10

Met Lys Lys Thr Thr Arg Leu Ile Ser Leu Ala Ile Val Leu Thr Leu
1               5                   10                  15

Leu Leu Thr Met Leu Val Pro Thr Asn Leu Tyr Ala Ala Ser Thr Val
            20                  25                  30

Thr Leu Asp Trp Asn Lys Glu Tyr Gln Val Ile Asp Gly Phe Gly Val
            35                  40                  45

Ser Glu Ala Phe His Gln Ser Asn Asn Ile Ala Leu Leu Gly Glu Thr
        50                  55                  60

Lys Gln Lys Glu Ile Tyr Asp Leu Leu Phe Ser Thr Glu Lys Gly Ala
65                  70                  75                  80

Gly Phe Ser Ile Phe Arg Ser Ile Leu Gly Asp Gly Thr Trp Gly
                85                  90                  95

Gly Ala Gln Asp Gly Pro Asn Lys Thr Met Gln Pro Ser Ala Asn Thr
            100                 105                 110

Trp Asp Trp Asn Glu Lys Asn Asp Asp Gln Ile Pro Met Tyr Arg Thr
        115                 120                 125

Ile Gln Glu Glu Tyr Gly Val Asp Lys Leu Leu Tyr Thr Val Trp Ser
    130                 135                 140

Pro Pro Ala Trp Met Lys Thr Asn Gly Ser Val Val Gly Gly Ser Leu
145                 150                 155                 160

Arg Ser Asp Met Tyr Gln Ala Tyr Ala Thr Tyr Leu Ala Glu Asn Ile
                165                 170                 175
```

Lys Asn Tyr Lys Ser Lys Phe Gly Ile Glu Ile Thr His Ile Gly Ile
            180                 185                 190

Gln Asn Glu Pro Asp Leu Glu Thr Ser Tyr Ser Ser Cys Lys Trp Thr
        195                 200                 205

Ala Ala Gln Phe Lys Thr Phe Met Lys Asp Tyr Leu Val Pro Thr Phe
    210                 215                 220

Asp Lys Glu Gly Ile Thr Ala Lys Val Val Met Ser Glu Asn Ser Gln
225                 230                 235                 240

Phe Asn Glu Ser Tyr Ala Val Asp Cys Leu Asn Asp Pro Val Ala Val
                245                 250                 255

Thr Arg Thr Asp Ile Val Gly Val His Asn Tyr Gly Asn Tyr Tyr Asn
            260                 265                 270

Thr Leu Pro Thr Thr Lys Ala Lys Gly Lys Gly Ile Trp Met Thr Glu
        275                 280                 285

Val Ser Asp Leu Asn Gly Asn Asp Leu Thr Ile Asn Asp Gly Leu Lys
    290                 295                 300

Trp Ala Lys Gln Val Tyr Asp Phe Met Thr Val Thr Gln Gly Asn Ala
305                 310                 315                 320

Trp Met Tyr Trp Trp Gly Ala Cys Tyr Lys Thr Trp Asn Gly Glu Gly
                325                 330                 335

Leu Ile Gln Met Asp Met Asn Ser Lys Asn Tyr Lys Val Gly Lys Arg
            340                 345                 350

Leu Phe Thr Ile Gly Gln Tyr Ser Arg Phe Val Arg Pro Gly Trp Val
        355                 360                 365

Arg Phe Asp Ala Thr Lys Asn Pro Val Ser Gly Val Tyr Val Thr Ala
    370                 375                 380

Tyr Lys Asp Pro Val Thr Gly Lys Phe Ala Val Val Ala Leu Asn Asp
385                 390                 395                 400

Gly Ser Ser Ser Gln Ser Ile Ser Tyr Asn Leu Gln Gly Phe Glu Ala
                405                 410                 415

Asp Ser Val Ile Pro Tyr Thr Thr Ser Ala Ser Gln Asp Leu Ala Ala
            420                 425                 430

Gly Ser Lys Ile Ser Ile Ser Gly Asn Ser Phe Thr Ala Thr Ile Pro
        435                 440                 445

Ala Lys Ser Val Val Thr Phe Val Gly Glu Thr Asn Ala Gly Val Tyr
    450                 455                 460

Gly Asp Val Asn Gly Asp Asn Ile Val Asp Ala Ile Asp Phe Ala Ile
465                 470                 475                 480

Ile Lys Gln Tyr Leu Met Gly Gln Ile Ser Thr Phe Pro Gly Lys Asn
                485                 490                 495

Gly Met Lys Leu Ala Asp Val Asn Asn Asp Gly Ser Val Asp Ala Ile
            500                 505                 510

Asp Phe Ala Thr Val Lys Met Phe Leu Leu Gly Asn Ile Ser Lys Leu
        515                 520                 525

Pro Val
    530

<210> SEQ ID NO 11
<211> LENGTH: 515
<212> TYPE: PRT
<213> ORGANISM: Artificial Sequence
<220> FEATURE:
<223> OTHER INFORMATION: Synthetic

<400> SEQUENCE: 11

Met Ala Ser Thr Val Thr Val Asp Trp Asp Thr Thr Tyr Gln Thr Ile
1               5                   10                  15

Asp Gly Phe Gly Val Ser Glu Ala Phe His Gln Ser Asn Asn Ile Ala
            20                  25                  30

Arg Leu Gly Glu Thr Lys Gln Asn Glu Ile Tyr Asp Leu Leu Phe Ser
        35                  40                  45

Thr Thr Asp Gly Ala Gly Phe Ser Ile Phe Arg Ser Ile Leu Gly Asp
    50                  55                  60

Gly Gly Thr Trp Gly Asn Ala Asp Asp Gly Pro Asn Lys Thr Met Gln
65              70                  75                  80

Pro Ala Glu Asp Val Trp Asp Trp Asn Glu Ser Asn Asp Asp Gln Ile
                85                  90                  95

Pro Met Ile Arg Ala Ile Gln Ser Lys Tyr Gly Val Asp Gln Ile Leu
            100                 105                 110

Tyr Thr Val Trp Ser Pro Pro Ala Trp Met Lys Thr Asn Gly Ser Val
        115                 120                 125

Val Gly Gly Ser Leu Arg Thr Asp Lys Tyr Gln Ala Tyr Ala Thr Tyr
130                 135                 140

Leu Ala Glu His Ile Lys Asn Tyr Lys Ser Lys Phe Gly Ile Glu Ile
145                 150                 155                 160

Thr His Ile Gly Ile Gln Asn Glu Pro Asn Leu Glu Thr Ser Tyr Ser
                165                 170                 175

Ser Cys Arg Trp Ser Pro Glu Glu Leu Arg Ile Phe Met Arg Asp Tyr
            180                 185                 190

Leu Val Pro Thr Phe Asp Lys Glu Asn Ile Thr Ala Lys Val Val Phe
        195                 200                 205

Ala Glu Asn Met Ser Phe Asn Glu Gln Tyr Ala Ile Asn Ser Leu Asn
    210                 215                 220

Asp Pro Ile Ala Val Lys Arg Val Asp Ile Val Gly Ala His Asn Tyr
225                 230                 235                 240

Gly Ser Ser Tyr Ile Pro Phe Thr Thr Thr Lys Ser Lys Gly Lys Gly
                245                 250                 255

Ile Trp Met Thr Glu Val Ser Asp Met Asn Gly Asn Asp Thr Thr Ile
            260                 265                 270

Asn Asp Gly Leu Arg Trp Ala Lys Glu Ile His Asp Phe Met Thr Ile
        275                 280                 285

Thr Glu Gly Asn Ala Trp Phe Tyr Trp Trp Gly Ala Cys Phe Lys Thr
    290                 295                 300

Tyr Asn Gly Glu Gly Leu Ile Gln Met Asp Leu Asn Ser Lys Thr Tyr
305                 310                 315                 320

Lys Val Ala Lys Arg Leu Tyr Thr Ile Gly Gln Phe Ser Arg Phe Ile
                325                 330                 335

Arg Pro Gly Trp Gln Arg Ile Glu Ala Thr Lys Asn Pro Val Ser Asn
            340                 345                 350

Val Tyr Val Thr Ala Tyr Lys Asp Pro Lys Thr Gly Lys Phe Ala Ile
        355                 360                 365

Val Ala Ile Asn Asn Gly Trp Ser Lys Gln Ser Ile Thr Tyr Thr Leu
    370                 375                 380

Lys Gly Phe Ser Pro Ala Ser Val Thr Pro Tyr Thr Thr Ser Ser Thr
385                 390                 395                 400

```
Gln Asn Leu Glu Lys Gly Ser Asp Ile Thr Val Asn Ser Ser Phe
            405                 410                 415

Ser Phe Glu Leu Ala Pro Asn Ser Ile Thr Thr Phe Val Gly Asp Thr
            420                 425                 430

Glu Ser Ala Ser Ile Ile Tyr Gly Asp Val Asn Gly Asp Gly Asp Val
            435                 440                 445

Asn Ser Ile Asp Tyr Gly Tyr Met Lys Trp Tyr Leu Leu Gly Gln Ile
450                 455                 460

Asn Ser Phe Pro Val Asp Asn Gly Asp Lys Val Ala Asp Leu Asp Gly
465                 470                 475                 480

Asp Gly Arg Ile Thr Ser Ile Asp Cys Ala Tyr Met Lys Met Tyr Leu
            485                 490                 495

Leu Gly Met Ile Gln Lys Phe Pro Val Glu Gln Leu Glu His His His
            500                 505                 510

His His His
        515

<210> SEQ ID NO 12
<211> LENGTH: 444
<212> TYPE: PRT
<213> ORGANISM: Artificial Sequence
<220> FEATURE:
<223> OTHER INFORMATION: Synthetic

<400> SEQUENCE: 12

Met Ala Ser Thr Val Thr Val Asp Trp Asp Thr Thr Tyr Gln Thr Ile
1               5                   10                  15

Asp Gly Phe Gly Val Ser Glu Ala Phe His Gln Ser Asn Asn Ile Ala
            20                  25                  30

Arg Leu Gly Glu Thr Lys Gln Asn Glu Ile Tyr Asp Leu Leu Phe Ser
        35                  40                  45

Thr Thr Asp Gly Ala Gly Phe Ser Ile Phe Arg Ser Ile Leu Gly Asp
    50                  55                  60

Gly Gly Thr Trp Gly Asn Ala Asp Asp Gly Pro Asn Lys Thr Met Gln
65                  70                  75                  80

Pro Ala Glu Asp Val Trp Asp Trp Asn Glu Ser Asn Asp Asp Gln Ile
                85                  90                  95

Pro Met Ile Arg Ala Ile Gln Ser Lys Tyr Gly Val Asp Gln Ile Leu
            100                 105                 110

Tyr Thr Val Trp Ser Pro Pro Ala Trp Met Lys Thr Asn Gly Ser Val
        115                 120                 125

Val Gly Gly Ser Leu Arg Thr Asp Lys Tyr Gln Ala Tyr Ala Thr Tyr
    130                 135                 140

Leu Ala Glu His Ile Lys Asn Tyr Lys Ser Lys Phe Gly Ile Glu Ile
145                 150                 155                 160

Thr His Ile Gly Ile Gln Asn Glu Pro Asn Leu Glu Thr Ser Tyr Ser
                165                 170                 175

Ser Cys Arg Trp Ser Pro Glu Glu Leu Arg Ile Phe Met Arg Asp Tyr
            180                 185                 190

Leu Val Pro Thr Phe Asp Lys Glu Asn Ile Thr Ala Lys Val Val Phe
        195                 200                 205

Ala Glu Asn Met Ser Phe Asn Glu Gln Tyr Ala Ile Asn Ser Leu Asn
    210                 215                 220

Asp Pro Ile Ala Val Lys Arg Val Asp Ile Val Gly Ala His Asn Tyr
225                 230                 235                 240
```

Gly Ser Ser Tyr Ile Pro Phe Thr Thr Thr Lys Ser Lys Lys Gly
            245                 250                 255

Ile Trp Met Thr Glu Val Ser Asp Met Asn Gly Asn Asp Thr Thr Ile
            260                 265                 270

Asn Asp Gly Leu Arg Trp Ala Lys Glu Ile His Asp Phe Met Thr Ile
            275                 280                 285

Thr Glu Gly Asn Ala Trp Phe Tyr Trp Trp Gly Ala Cys Phe Lys Thr
        290                 295                 300

Tyr Asn Gly Glu Gly Leu Ile Gln Met Asp Leu Asn Ser Lys Thr Tyr
305                 310                 315                 320

Lys Val Ala Lys Arg Leu Tyr Thr Ile Gly Gln Phe Ser Arg Phe Ile
                325                 330                 335

Arg Pro Gly Trp Gln Arg Ile Glu Ala Thr Lys Asn Pro Val Ser Asn
            340                 345                 350

Val Tyr Val Thr Ala Tyr Lys Asp Pro Lys Thr Gly Lys Phe Ala Ile
            355                 360                 365

Val Ala Ile Asn Asn Gly Trp Ser Lys Gln Ser Ile Thr Tyr Thr Leu
    370                 375                 380

Lys Gly Phe Ser Pro Ala Ser Val Thr Pro Tyr Thr Thr Ser Ser Thr
385                 390                 395                 400

Gln Asn Leu Glu Lys Gly Ser Asp Ile Thr Val Asn Ser Ser Phe
                405                 410                 415

Ser Phe Glu Leu Ala Pro Asn Ser Ile Thr Thr Phe Val Gly Asp Thr
            420                 425                 430

Glu Ser Ala Ser Leu Glu His His His His His
            435                 440

<210> SEQ ID NO 13
<211> LENGTH: 439
<212> TYPE: PRT
<213> ORGANISM: Artificial Sequence
<220> FEATURE:
<223> OTHER INFORMATION: Synthetic

<400> SEQUENCE: 13

Met Ala Ser Thr Val Thr Leu Asp Trp Asp Thr Asn Tyr Gln Asn Ile
1               5                   10                  15

Asp Gly Phe Gly Val Ser Glu Ala Phe His Gln Ser Asn Asn Ile Ala
            20                  25                  30

Leu Leu Gly Asp Thr Lys Lys Asn Glu Ile Tyr Asp Leu Leu Phe Ser
        35                  40                  45

Thr Thr Lys Gly Ala Gly Phe Ser Ile Phe Arg Ser Ile Leu Gly Asp
    50                  55                  60

Gly Gly Thr Trp Gly Asn Ala Glu Asp Gly Pro Asn Lys Thr Met Gln
65                  70                  75                  80

Pro Ser Glu Thr Thr Trp Asp Trp Lys Glu Ser Asn Asp Asp Gln Ile
                85                  90                  95

Pro Met Tyr Lys Glu Ile Arg Glu Lys Tyr Gly Ile Asp Lys Leu Leu
            100                 105                 110

Tyr Thr Ala Trp Ser Pro Pro Ala Trp Met Lys Ser Asn Gly Ser Thr
        115                 120                 125

Ser Arg Gly Thr Ile Lys Ala Asp Lys Tyr Gln Ala Tyr Ala Thr Tyr
    130                 135                 140

Leu Ala Glu His Ile Lys Asn Tyr Lys Ser Lys Phe Gly Ile Asp Ile
145                 150                 155                 160

Thr His Ile Gly Ile Ser Asn Glu Pro Asn Leu Glu Thr Asn Tyr Ser
                165                 170                 175

Ser Cys Thr Trp Ser Ser Ser Gln Phe Lys Thr Phe Met Lys Asp Tyr
            180                 185                 190

Leu Val Pro Thr Phe Asp Lys Glu Asn Ile Thr Ala Lys Val Ile Met
        195                 200                 205

Gly Glu Pro Met Ala Cys Thr Glu Ser Phe Ala Ile Asp Ser Leu Asn
    210                 215                 220

Asp Ala Thr Ala Ser Lys Arg Thr Asp Ile Val Gly Cys His Asn Tyr
225                 230                 235                 240

Gly Ser Thr Tyr Val Ala Phe Pro Thr Thr Lys Ser Lys Gly Lys Gly
                245                 250                 255

Ile Trp Met Thr Glu Val Ser Asp Met Asn Gly Asn Asp Ile Thr Ile
                260                 265                 270

Asn Asp Gly Leu Lys Trp Ala Lys Glu Val His Asp Phe Met Thr Ile
            275                 280                 285

Thr Gln Gly Asn Ser Trp Ser Tyr Trp Trp Gly Ala Cys Tyr Lys Thr
        290                 295                 300

His Asn Gly Glu Gly Leu Ile Gln Met Asn Met Gly Ala Lys Thr Tyr
305                 310                 315                 320

Thr Val Ala Lys Arg Leu Tyr Thr Ile Gly Gln Tyr Ala Arg Phe Ile
                325                 330                 335

Arg Pro Glu Trp Gln Arg Phe Ser Ala Thr Ala Ser Pro Val Ser Gly
                340                 345                 350

Val Tyr Val Thr Ala Tyr Lys Asp Pro Ala Thr Gly Glu Phe Ala Val
            355                 360                 365

Val Ala Ile Asn Asn Gly Ser Ser Asp Gln Ser Val Ser Phe Asn Leu
        370                 375                 380

Lys Gly Phe Thr Ala Ser Ala Val Thr Pro Tyr Thr Thr Ser Ala Ser
385                 390                 395                 400

Gln Asn Leu Ala Glu Gly Ser Ser Ile Ala Val Ser Gly Ser Ser Phe
                405                 410                 415

Thr Gly Asn Leu Pro Ala Lys Ser Val Thr Thr Phe Val Gly Ala Leu
            420                 425                 430

Glu His His His His His His
        435

<210> SEQ ID NO 14
<211> LENGTH: 630
<212> TYPE: PRT
<213> ORGANISM: Clostridium thermocellum

<400> SEQUENCE: 14

Met Arg Lys Leu Arg Lys Leu Leu Phe Ser Thr Val Leu Phe Val
1               5                   10                  15

Val Phe Thr Gln Leu Phe Gly Phe Ile Ile Thr Val Asp Ala Ala Glu
            20                  25                  30

Thr Ala Thr Ile Asn Leu Ser Ala Glu Lys Gln Val Ile Arg Gly Phe
        35                  40                  45

Gly Gly Met Asn His Pro Val Trp Ile Ser Asp Leu Thr Pro Gln Gln
    50                  55                  60

Arg Asp Thr Ala Phe Gly Asn Gly Glu Gly Gln Leu Gly Phe Thr Ile
65                  70                  75                  80

```
Leu Arg Ile His Val Asp Glu Asn Arg Asn Trp Ser Lys Glu Val
            85                  90                  95

Ala Thr Ala Arg Arg Ala Ile Glu Leu Gly Ala Ile Val Phe Ala Ser
                100                 105                 110

Pro Trp Asn Pro Pro Ser Asn Met Val Glu Thr Phe Thr Arg Asn Gly
        115                 120                 125

Val Pro Asn Gln Lys Arg Leu Arg Tyr Asp Lys Tyr Gly Asp Tyr Val
    130                 135                 140

Gln His Leu Asn Asp Phe Val Ala Tyr Met Lys Ser Asn Gly Val Asp
145                 150                 155                 160

Leu Tyr Ala Ile Ser Val Gln Asn Glu Pro Asp Tyr Ala His Glu Trp
                165                 170                 175

Thr Trp Trp Thr Pro Gln Glu Met Leu Arg Phe Met Arg Asp Tyr Ala
            180                 185                 190

Gly Gln Ile Asn Cys Arg Val Met Ala Pro Glu Ser Phe Gln Tyr Leu
        195                 200                 205

Lys Asn Met Ser Asp Pro Ile Leu Asn Asp Pro Gln Ala Leu Ala Asn
    210                 215                 220

Leu Asp Ile Leu Gly Ala His Phe Tyr Gly Thr Thr Val Asn Asn Met
225                 230                 235                 240

Pro Tyr Pro Leu Phe Glu Gln Lys Gly Ala Gly Lys Glu Leu Trp Met
                245                 250                 255

Thr Glu Val Tyr Val Pro Asn Ser Asp Ser Asn Ser Ala Asp Arg Trp
            260                 265                 270

Pro Glu Ala Leu Glu Val Ala His Asn Met His Asn Ala Leu Val Glu
        275                 280                 285

Gly Asn Phe Gln Ala Tyr Val Trp Trp Tyr Ile Arg Arg Ser Tyr Gly
    290                 295                 300

Pro Met Lys Glu Asp Gly Thr Ile Ser Lys Arg Gly Tyr Met Met Ala
305                 310                 315                 320

His Tyr Ser Lys Phe Val Arg Pro Gly Tyr Val Arg Val Asp Ala Thr
                325                 330                 335

Lys Asn Pro Thr Tyr Asn Val Tyr Leu Ser Ala Tyr Lys Asn Lys Lys
            340                 345                 350

Asp Asn Ser Val Val Ala Val Val Ile Asn Lys Ser Thr Glu Ala Lys
        355                 360                 365

Thr Ile Asn Ile Ser Val Pro Gly Thr Ser Ile Arg Lys Trp Glu Arg
    370                 375                 380

Tyr Val Thr Thr Gly Ser Lys Asn Leu Arg Lys Glu Ser Asp Ile Asn
385                 390                 395                 400

Ala Ser Gly Thr Thr Phe Gln Val Thr Leu Glu Pro Gln Ser Val Thr
                405                 410                 415

Thr Phe Val Gly Gly Ser Ser Glu Pro Gln Ile Pro Val Glu Arg
            420                 425                 430

Asn Ala Phe Ser Lys Ile Glu Cys Glu Glu Tyr Asn Ala Thr Asn Ser
        435                 440                 445

Ser Thr Val Gln Val Val Gly Thr Gly Thr Gly Ser Gly Leu Gly Tyr
    450                 455                 460

Ile Glu Asn Gly Asn Tyr Phe Ala Tyr Lys Asn Ile Asn Phe Gly Asn
465                 470                 475                 480

Gly Ala Asn Ser Phe Lys Ile Arg Ala Ala Thr Thr Gly Thr Pro Lys
                485                 490                 495
```

```
Ile Glu Ile Arg Leu Gly Ser Pro Gly Thr Leu Ala Gly Thr Leu
            500                 505                 510

Gln Val Ala Ala Thr Gly Gly Phe Asn Ala Tyr Glu Glu Gln Ser Cys
        515                 520                 525

Ser Ile Asn Lys Ile Thr Gly Val Gln Asp Val Tyr Leu Val Phe Gly
        530                 535                 540

Gly Ala Val Asn Val Asp Trp Phe Thr Phe Glu Ser Lys Gln Glu Pro
545                 550                 555                 560

Thr Phe Lys Tyr Gly Asp Leu Asn Gly Asp Gly Asn Val Asn Ser Thr
            565                 570                 575

Asp Ser Thr Leu Met Ser Arg Tyr Leu Leu Gly Ile Ile Thr Thr Leu
        580                 585                 590

Pro Ala Gly Glu Lys Ala Ala Asp Leu Asn Gly Asp Gly Lys Val Asn
        595                 600                 605

Ser Thr Asp Tyr Asn Ile Leu Lys Arg Tyr Leu Leu Lys Tyr Ile Asp
        610                 615                 620

Lys Phe Pro Val Glu Ser
625                 630

<210> SEQ ID NO 15
<211> LENGTH: 422
<212> TYPE: PRT
<213> ORGANISM: Bacillus subtilis

<400> SEQUENCE: 15

Met Ile Pro Arg Ile Lys Lys Thr Ile Cys Val Leu Leu Val Cys Phe
1               5                   10                  15

Thr Met Leu Ser Val Met Leu Gly Pro Gly Ala Thr Glu Val Leu Ala
            20                  25                  30

Ala Ser Asp Val Thr Val Asn Val Ser Ala Glu Lys Gln Val Ile Arg
        35                  40                  45

Gly Phe Gly Gly Met Asn His Pro Ala Trp Ala Gly Asp Leu Thr Ala
    50                  55                  60

Ala Gln Arg Glu Thr Ala Phe Gly Asn Gly Gln Asn Gln Leu Gly Phe
65                  70                  75                  80

Ser Ile Leu Arg Ile His Val Asp Glu Asn Arg Asn Asn Trp Tyr Lys
            85                  90                  95

Glu Val Glu Thr Ala Lys Ser Ala Val Lys His Gly Ala Ile Val Phe
        100                 105                 110

Ala Ser Pro Trp Asn Pro Pro Ser Asp Met Val Glu Thr Phe Asn Arg
        115                 120                 125

Asn Gly Asp Thr Ser Ala Lys Arg Leu Lys Tyr Asn Lys Tyr Ala Ala
    130                 135                 140

Tyr Ala Gln His Leu Asn Asp Phe Val Thr Phe Met Lys Asn Asn Gly
145                 150                 155                 160

Val Asn Leu Tyr Ala Ile Ser Val Gln Asn Glu Pro Asp Tyr Ala His
            165                 170                 175

Glu Trp Thr Trp Trp Thr Pro Gln Glu Ile Leu Arg Phe Met Arg Glu
        180                 185                 190

Asn Ala Gly Ser Ile Asn Ala Arg Val Ile Ala Pro Glu Ser Phe Gln
        195                 200                 205

Tyr Leu Lys Asn Leu Ser Asp Pro Ile Leu Asn Asp Pro Gln Ala Leu
    210                 215                 220

Ala Asn Met Asp Ile Leu Gly Thr His Leu Tyr Gly Thr Gln Val Ser
225                 230                 235                 240
```

```
Gln Phe Pro Tyr Pro Leu Phe Lys Gln Lys Gly Ala Gly Lys Asp Leu
                245                 250                 255

Trp Met Thr Glu Val Tyr Tyr Pro Asn Ser Asp Thr Asn Ser Ala Asp
            260                 265                 270

Arg Trp Pro Glu Ala Leu Asp Val Ser Gln His Ile His Asn Ala Met
        275                 280                 285

Val Glu Gly Asp Phe Gln Ala Tyr Val Trp Trp Tyr Ile Arg Arg Ser
    290                 295                 300

Tyr Gly Pro Met Lys Glu Asp Gly Thr Ile Ser Lys Arg Gly Tyr Asn
305                 310                 315                 320

Met Ala His Phe Ser Lys Phe Val Arg Pro Gly Tyr Val Arg Ile Asp
                325                 330                 335

Ala Thr Lys Asn Pro Asn Ala Asn Val Tyr Val Ser Ala Tyr Lys Gly
            340                 345                 350

Asp Asn Lys Val Val Ile Val Ala Ile Asn Lys Ser Asn Thr Gly Val
        355                 360                 365

Asn Gln Asn Phe Val Leu Gln Asn Gly Ser Ala Ser Asn Val Ser Arg
    370                 375                 380

Trp Ile Thr Ser Ser Ser Asn Leu Gln Pro Gly Thr Asn Leu Thr
385                 390                 395                 400

Val Ser Gly Asn His Phe Trp Ala His Leu Pro Ala Gln Ser Val Thr
                405                 410                 415

Thr Phe Val Val Asn Arg
            420

<210> SEQ ID NO 16
<211> LENGTH: 588
<212> TYPE: PRT
<213> ORGANISM: Clostridium acetobutylicum

<400> SEQUENCE: 16

Met Lys Asn Lys Ile Lys Lys Ile Val Leu Ser Val Val Thr Phe Ser
1               5                   10                  15

Met Ile Cys Leu Pro Phe Thr Asp Gly Phe Thr Ser Ile Lys Ala Ala
            20                  25                  30

Ser Asn Val Met Val Asn Leu Ala Ser Lys Lys Gln Val Ile Arg Gly
        35                  40                  45

Phe Gly Gly Met Asn Ser Val Ala Trp Ala Gly Asp Leu Thr Ala Ala
    50                  55                  60

Gln Arg Glu Thr Ala Phe Gly Asn Gly Asn Asn Gln Leu Gly Leu Ser
65                  70                  75                  80

Val Val Arg Ile Phe Val Asp Asp Asn Lys Asn Asn Trp Tyr Lys Glu
                85                  90                  95

Leu Pro Thr Ala Lys Ser Ala Ile Ala His Gly Ser Ile Val Phe Ala
            100                 105                 110

Thr Pro Trp Asn Pro Pro Ser Ser Met Thr Glu Thr Phe Asn Arg Asn
        115                 120                 125

Gly Glu Lys Ala Lys Arg Leu Arg Tyr Asp Lys Tyr Gly Asp Tyr Ala
    130                 135                 140

Lys Tyr Leu Asn Asp Phe Val Ser Tyr Met Lys Asn Asn Gly Val Asn
145                 150                 155                 160

Leu Tyr Ala Ile Ser Val Gln Asn Glu Pro Asp Tyr Gly Arg Asp Trp
                165                 170                 175
```

```
Thr Trp Trp Thr Pro Gln Glu Val Leu Arg Phe Met Arg Asp Tyr Ala
            180                 185                 190

Gly Ser Ile Asn Cys Arg Val Met Ser Pro Glu Ser Phe Ser Tyr Gln
        195                 200                 205

Lys Asn Met Tyr Asp Pro Ile Leu Asn Asp Pro Lys Ala Leu Ala Asn
    210                 215                 220

Met Asp Ile Leu Gly Thr His Thr Tyr Gly Thr Gln Val Lys Asp Phe
225                 230                 235                 240

Pro Tyr Pro Leu Phe Lys Gln Lys Ala Ala Gly Lys Asp Leu Trp Met
                245                 250                 255

Thr Glu Val Tyr Val Pro Asn Ser Asp Ala Asn Ser Ala Asp Arg Trp
            260                 265                 270

Pro Glu Ala Leu Glu Val Ala Asn His Ile Asn Asn Ala Met Val Glu
        275                 280                 285

Gly Asp Phe Gln Ala Tyr Val Trp Trp Tyr Ile Arg Arg Ser Tyr Gly
    290                 295                 300

Leu Ile Lys Glu Asn Gly Ala Ile Ser Lys Arg Gly Tyr Met Met Ala
305                 310                 315                 320

His Phe Ser Lys Phe Val Arg Pro Gly Tyr Val Arg Val Asp Ala Thr
                325                 330                 335

Lys Asn Pro Val Gly Asn Val Tyr Val Ser Ala Tyr Thr Gly Asn Asn
            340                 345                 350

Lys Val Val Ile Val Ala Ile Asn Lys Gly Thr Tyr Pro Val Asn Gln
        355                 360                 365

Ser Phe Asn Ile Gln Asn Ser Thr Val Ser Asn Val Ser Ser Trp Val
    370                 375                 380

Thr Ser Gly Thr Leu Asn Met Ala Lys Thr Asn Ser Asn Ile Asn Ala
385                 390                 395                 400

Ala Asn Gly Arg Phe Asn Ala Ser Leu Pro Ala Gln Ser Val Thr Thr
                405                 410                 415

Phe Val Ala Asp Leu Asn Ser Thr Lys Pro Thr Thr Asn Pro Thr Thr
            420                 425                 430

Asn Pro Thr Pro Gly Ser Thr Val Thr Leu Asn Asn Gly Trp Tyr Tyr
        435                 440                 445

Ile Lys Asn Ile Asn Ala Gln Lys Tyr Leu Gln Val Ala Asn Asn Thr
    450                 455                 460

Gly Lys Ala Gly Gln Asn Val Glu Leu Gly Ser Gly Ser Gly Val Ala
465                 470                 475                 480

Gly Gln Lys Trp Tyr Leu Thr Asn Thr Gly Asp Gly Tyr Ile Thr Leu
                485                 490                 495

Lys Asn Ala Leu Gly Asn Tyr Met Leu Asp Val Ser Tyr Gly Glu Asn
            500                 505                 510

Lys Asp Gly Ser Asn Ile Gln Ile Phe Asn Ala Tyr Ser Gly Asp Ser
        515                 520                 525

Gln Lys Phe Ala Val Lys Ala Ser Ser Lys Asn Gly Gln Tyr Ser Val
    530                 535                 540

Ala Thr Lys Ser Ser Asn Gly Ser Lys Val Leu Asp Asp Tyr Asn Phe
545                 550                 555                 560

Gly Thr Ala Asp Gly Thr Asn Val Cys Gln Trp Thr Tyr Gly Gly Asn
                565                 570                 575

Ala Asn Gln Leu Trp Val Phe Glu Pro Thr Asn Asn
            580                 585
```

<210> SEQ ID NO 17
<211> LENGTH: 413
<212> TYPE: PRT
<213> ORGANISM: Dickeya dadantii

<400> SEQUENCE: 17

```
Met Asn Gly Asn Val Ser Leu Trp Val Arg His Cys Leu His Ala Ala
1               5                   10                  15

Leu Phe Val Ser Ala Thr Ala Gly Ser Phe Ser Val Tyr Ala Asp Thr
            20                  25                  30

Val Lys Ile Asp Ala Asn Val Asn Tyr Gln Ile Ile Gln Gly Phe Gly
        35                  40                  45

Gly Met Ser Gly Val Gly Trp Ile Asn Asp Leu Thr Thr Glu Gln Ile
    50                  55                  60

Asn Thr Ala Tyr Gly Ser Gly Val Gly Gln Ile Gly Leu Ser Ile Met
65                  70                  75                  80

Arg Val Arg Ile Asp Pro Asp Ser Ser Lys Trp Asn Ile Gln Leu Pro
                85                  90                  95

Ser Ala Arg Gln Ala Val Ser Leu Gly Ala Lys Ile Met Ala Thr Pro
            100                 105                 110

Trp Ser Pro Pro Ala Tyr Met Lys Ser Asn Asn Ser Leu Ile Asn Gly
        115                 120                 125

Gly Arg Leu Leu Pro Ala Asn Tyr Ser Ala Tyr Thr Ser His Leu Leu
    130                 135                 140

Asp Phe Ser Lys Tyr Met Gln Thr Asn Gly Ala Pro Leu Tyr Ala Ile
145                 150                 155                 160

Ser Ile Gln Asn Glu Pro Asp Trp Lys Pro Asp Tyr Glu Ser Cys Glu
                165                 170                 175

Trp Ser Gly Asp Glu Phe Lys Ser Tyr Leu Lys Ser Gln Gly Ser Lys
            180                 185                 190

Phe Gly Ser Leu Lys Val Ile Val Ala Glu Ser Leu Gly Phe Asn Pro
        195                 200                 205

Ala Leu Thr Asp Pro Val Leu Lys Asp Ser Asp Ala Ser Lys Tyr Val
    210                 215                 220

Ser Ile Ile Gly Gly His Leu Tyr Gly Thr Thr Pro Lys Pro Tyr Pro
225                 230                 235                 240

Leu Ala Gln Asn Ala Gly Lys Gln Leu Trp Met Thr Glu His Tyr Val
                245                 250                 255

Asp Ser Lys Gln Ser Ala Asn Asn Trp Thr Ser Ala Ile Glu Val Gly
            260                 265                 270

Thr Glu Leu Asn Ala Ser Met Val Ser Asn Tyr Ser Ala Tyr Val Trp
        275                 280                 285

Trp Tyr Ile Arg Arg Ser Tyr Gly Leu Leu Thr Glu Asp Gly Lys Val
    290                 295                 300

Ser Lys Arg Gly Tyr Val Met Ser Gln Tyr Ala Arg Phe Val Arg Pro
305                 310                 315                 320

Gly Ala Leu Arg Ile Gln Ala Thr Glu Asn Pro Gln Ser Asn Val His
                325                 330                 335

Leu Thr Ala Tyr Lys Asn Thr Asp Gly Lys Met Val Ile Val Ala Val
            340                 345                 350

Asn Thr Asn Asp Ser Asp Gln Met Leu Ser Leu Asn Ile Ser Asn Ala
        355                 360                 365

Asn Val Thr Lys Phe Glu Lys Tyr Ser Thr Ser Ala Ser Leu Asn Val
    370                 375                 380
```

Glu Tyr Gly Gly Ser Ser Gln Val Asp Ser Ser Gly Lys Ala Thr Val
385                 390                 395                 400

Trp Leu Asn Pro Leu Ser Val Thr Thr Phe Val Ser Lys
            405                 410

<210> SEQ ID NO 18
<211> LENGTH: 401
<212> TYPE: PRT
<213> ORGANISM: Xanthomonas campestris

<400> SEQUENCE: 18

Met Leu Leu Arg Ala Val Val Pro Leu Ile Gly Leu Cys Leu Thr Ala
1               5                   10                  15

Thr Ala Ala Ala Gln Thr Val Thr Val Asn Pro Asn Gln Ala Tyr Gln
                20                  25                  30

Thr Val Arg Gly Phe Gly Gly Met Asn Gly Ala Gly Trp Ile Asn Asp
            35                  40                  45

Leu Thr Pro Ala Gln Val Asp Leu Ala Tyr Gly Ser Gly Asn Gly Gln
50                  55                  60

Ile Gly Leu Ser Ile Leu Arg Met Arg Ile Asp Pro Ser Ser Ser Gly
65                  70                  75                  80

Trp Ser Leu Gln Val Pro Thr Ala Ala Arg Val Arg Ala Leu Gly Gly
                85                  90                  95

Ile Leu Phe Ala Thr Pro Trp Ser Pro Pro Ala Tyr Met Lys Ser Asn
            100                 105                 110

Asn Ser Leu Val Asn Gly Gly Lys Leu Leu Ser Thr Ser Tyr Ala Ala
        115                 120                 125

Tyr Thr Thr His Leu Leu Asp Phe Ala Asn Tyr Leu Ser Ala Arg Asn
    130                 135                 140

Ala Pro Leu Tyr Ala Ile Ser Leu Gln Asn Glu Pro Asp Trp His Pro
145                 150                 155                 160

Asp Tyr Glu Ser Ala Asp Trp Asn Gly Ser Asp Phe Val Asn Tyr Leu
                165                 170                 175

Asn Ala Glu Gly Gly Lys Phe Gly Ala Leu Lys Val Ile Val Gly Glu
            180                 185                 190

Leu Val Gly Phe Thr Phe Ser Ile Thr Asp Pro Val Leu Asn Asn Ala
        195                 200                 205

Lys Ala Ser Gln Ala Thr Ser Ile Val Ala Gly His Leu Tyr Gly Ala
210                 215                 220

Gln Pro Lys Asp Tyr Ala Leu Ala Arg Ser Lys Gly Lys Gln Val Trp
225                 230                 235                 240

Met Thr Glu His Tyr Thr Asp Thr Ser Asp Gly Asn Ala Trp Pro Ser
                245                 250                 255

Ala Leu Gly Val Ala Ser Glu Leu His Gln Ser Met Val Ala Asn Tyr
            260                 265                 270

Asn Ala Tyr Ile Trp Trp Tyr Ile Arg Arg Ser Tyr Gly Leu Ile Ser
        275                 280                 285

Glu Gly Gly Ser Val Ser Lys Arg Gly Tyr Val Met Ser Gln Phe Ala
    290                 295                 300

Arg Phe Val Arg Pro Gly Ser Val Arg Ile Gly Ala Thr Glu His Pro
305                 310                 315                 320

Tyr Ala Asp Val Ser Thr Thr Ala Tyr Arg Thr Pro Asn Lys Ile
                325                 330                 335

```
Val Val Val Ala Val Asn Thr Gly Thr Ala His Gln Arg Leu Asp Leu
                340                 345                 350

Thr Val Pro Ala Gly Ala Ala Thr Gln Phe Val Lys Tyr Thr Thr Ser
            355                 360                 365

Ser Ser Leu Asn Ala Gly Tyr Ala Gly Ala Tyr Thr Val Ser Gly Gly
        370                 375                 380

Lys Thr Ser Leu Tyr Ile Asp Pro Gln Ser Ile Ala Thr Leu Val Gly
385                 390                 395                 400

Gln

<210> SEQ ID NO 19
<211> LENGTH: 546
<212> TYPE: PRT
<213> ORGANISM: Bacteroides cellulosilyticus

<400> SEQUENCE: 19

Met Lys Leu Phe Ile Arg Asn Leu Cys Ile Phe Leu Met Gly Met Ser
1               5                   10                  15

Cys Trp Ala Cys Ser Asp Asn Asn Ala Glu Thr Asp Asp Asn Gly
            20                  25                  30

Lys Gly Ala Tyr Ala Leu Phe Leu Lys Lys Ser Ile Thr Val Ser Ala
        35                  40                  45

Gly Glu Asn Gln Thr Glu Val Val Ile Glu Trp Ala Lys Thr Ser Trp
    50                  55                  60

Glu Ile Thr Phe Glu Gln Gly Asp Ile Val Lys Ser Ile Thr Pro Met
65                  70                  75                  80

Ser Gly Gly Ser Ser Asp Gly Glu Lys Gln Tyr Thr Lys Ile Gln Val
                85                  90                  95

Val Cys Asn Ala Asn Ala Ser Met Lys Gln Arg Thr Gln Thr Ile His
            100                 105                 110

Ile Thr Asp Leu Thr Asn Lys Gln Thr Thr Asp Leu Leu Ile Glu Gln
        115                 120                 125

Glu Pro Ala Phe Lys Ser Val Thr Leu Asn Ile Asp Pro Thr Val Lys
    130                 135                 140

Tyr Gln Pro Ile Ala Gly Phe Gly Gly Met Tyr Asn Pro Lys Ile Trp
145                 150                 155                 160

Cys Gly Gly Asn Leu Ile Ser Ala Arg Gln Leu Asp Gln Met Tyr Gly
                165                 170                 175

Glu Gly Gly Leu Gly Tyr Ser Ile Leu Arg Leu Met Val Tyr Pro Asn
            180                 185                 190

Glu Ser Asp Trp Asn Ala Asp Val Glu Ala Ala Lys Ala Ala Gln Ala
        195                 200                 205

Asn Gly Ala Ile Val Phe Ala Cys Pro Trp Asp Cys Thr Asp Ala Leu
    210                 215                 220

Ser Glu Gln Ile Lys Val Asn Gly Lys Glu Val Lys His Leu Lys Lys
225                 230                 235                 240

Glu Asn Tyr Gly Ala Tyr Ala Asp His Leu Ile Arg Tyr Ile Asn Phe
                245                 250                 255

Met Lys Gln Asn Gly Val Asp Leu Tyr Ala Ile Ser Val Gln Asn Glu
            260                 265                 270

Pro Asp Met Asp Phe Thr Tyr Trp Thr Pro Gln Glu Val Val Asp Phe
        275                 280                 285

Val Lys Gln Tyr Gly Ala Lys Ile Arg Glu Thr Gly Val Arg Leu Met
    290                 295                 300
```

-continued

Ser Pro Glu Ala Cys Gly Thr Pro Glu Tyr Thr Asp Leu Ile Ile
305                 310                 315                 320

Asn Asp Ala Gly Ala Phe Ala Gln Thr Asp Ile Ile Ala Gly His Leu
            325                 330                 335

Tyr Gln Gly Phe Thr Asp Leu Asp Asn Gly Tyr Val Lys Asn Arg His
        340                 345                 350

Asp Tyr Ile Cys Gly Leu Tyr Pro Arg Ile His Gly Lys Thr Trp Trp
    355                 360                 365

Met Thr Glu His Leu Phe Asn Asp Gly Glu Lys Ser Asp Asp Pro Ser
370                 375                 380

Ala Trp Glu Phe Gln Lys Trp Gln Tyr Cys Leu Asn His Leu Gly Lys
385                 390                 395                 400

Glu Ile His Met Cys Met Glu Gly Tyr Cys Ser Ala Tyr Val Tyr Trp
                405                 410                 415

Tyr Leu Lys Arg Phe Tyr Gly Leu Met Gly Asp Asn Asp Lys Arg Ser
            420                 425                 430

Pro Val Gly Glu Gly Ile Ala Lys Asn Gly Tyr Ile Met Ala His
        435                 440                 445

Tyr Ala Gln Tyr Ala Thr Gly Thr Thr Arg Ile Lys Ala Val Thr Asn
450                 455                 460

Asn Thr Gly Ile Cys Ala Thr Ala Tyr Ile Asn Glu Thr Gly Asn Glu
465                 470                 475                 480

Val Thr Val Val Leu Leu Asn Phe Thr Gly Ala Thr Gln Cys Ile Glu
                485                 490                 495

Ile Pro Leu Ala Gly Met Lys Arg Ala Asn Ala Val Glu Thr Asn Glu
            500                 505                 510

Asn Lys Asn Met Glu Val Ile Ser Thr Glu Met Leu Glu Ser Gly Glu
        515                 520                 525

Gly Val Tyr Val Leu Leu Ser Gly Asn Ser Ile Val Ser Val Arg Leu
    530                 535                 540

Thr Leu
545

<210> SEQ ID NO 20
<211> LENGTH: 534
<212> TYPE: PRT
<213> ORGANISM: Artificial Sequence
<220> FEATURE:
<223> OTHER INFORMATION: Synthetic

<400> SEQUENCE: 20

Met Ala Cys Ser Asp Asn Asn Ala Glu Thr Asp Asp Asn Gly Lys
1               5                   10                  15

Gly Ala Tyr Ala Leu Phe Leu Lys Lys Ser Ile Thr Val Ser Ala Gly
            20                  25                  30

Glu Asn Gln Thr Glu Val Val Ile Glu Trp Ala Lys Thr Ser Trp Glu
        35                  40                  45

Ile Thr Phe Glu Gln Gly Asp Ile Val Lys Ser Ile Thr Pro Met Ser
    50                  55                  60

Gly Gly Ser Ser Asp Gly Glu Lys Gln Tyr Thr Lys Ile Gln Val Val
65                  70                  75                  80

Cys Asn Ala Asn Ala Ser Met Lys Gln Arg Thr Gln Thr Ile His Ile
                85                  90                  95

Thr Asp Leu Thr Asn Lys Gln Thr Thr Asp Leu Leu Ile Glu Gln Glu
            100                 105                 110

```
Pro Ala Phe Lys Ser Val Thr Leu Asn Ile Asp Pro Thr Val Lys Tyr
            115                 120                 125

Gln Pro Ile Ala Gly Phe Gly Gly Met Tyr Asn Pro Lys Ile Trp Cys
130                 135                 140

Gly Gly Asn Leu Ile Ser Ala Arg Gln Leu Asp Gln Met Tyr Gly Glu
145                 150                 155                 160

Gly Gly Leu Gly Tyr Ser Ile Leu Arg Leu Met Val Tyr Pro Asn Glu
                165                 170                 175

Ser Asp Trp Asn Ala Asp Val Glu Ala Lys Ala Ala Gln Ala Asn
            180                 185                 190

Gly Ala Ile Val Phe Ala Cys Pro Trp Asp Cys Thr Asp Ala Leu Ser
            195                 200                 205

Glu Gln Ile Lys Val Asn Gly Lys Glu Val Lys His Leu Lys Lys Glu
            210                 215                 220

Asn Tyr Gly Ala Tyr Ala Asp His Leu Ile Arg Tyr Ile Asn Phe Met
225                 230                 235                 240

Lys Gln Asn Gly Val Asp Leu Tyr Ala Ile Ser Val Gln Asn Glu Pro
                245                 250                 255

Asp Met Asp Phe Thr Tyr Trp Thr Pro Gln Glu Val Val Asp Phe Val
            260                 265                 270

Lys Gln Tyr Gly Ala Lys Ile Arg Glu Thr Gly Val Arg Leu Met Ser
                275                 280                 285

Pro Glu Ala Cys Gly Thr Pro Pro Glu Tyr Thr Asp Leu Ile Ile Asn
            290                 295                 300

Asp Ala Gly Ala Phe Ala Gln Thr Asp Ile Ile Ala Gly His Leu Tyr
305                 310                 315                 320

Gln Gly Phe Thr Asp Leu Asp Asn Gly Tyr Val Lys Asn Arg His Asp
                325                 330                 335

Tyr Ile Cys Gly Leu Tyr Pro Arg Ile His Gly Lys Thr Trp Trp Met
                340                 345                 350

Thr Glu His Leu Phe Asn Asp Gly Glu Lys Ser Asp Asp Pro Ser Ala
            355                 360                 365

Trp Glu Phe Gln Lys Trp Gln Tyr Cys Leu Asn His Leu Gly Lys Glu
            370                 375                 380

Ile His Met Cys Met Glu Gly Tyr Cys Ser Ala Tyr Val Tyr Trp Tyr
385                 390                 395                 400

Leu Lys Arg Phe Tyr Gly Leu Met Gly Asp Asn Asp Lys Arg Ser Pro
                405                 410                 415

Val Gly Glu Gly Glu Ile Ala Lys Asn Gly Tyr Ile Met Ala His Tyr
            420                 425                 430

Ala Gln Tyr Ala Thr Gly Thr Thr Arg Ile Lys Ala Val Thr Asn Asn
                435                 440                 445

Thr Gly Ile Cys Ala Thr Ala Tyr Ile Asn Glu Thr Gly Asn Glu Val
            450                 455                 460

Thr Val Val Leu Leu Asn Phe Thr Gly Ala Thr Gln Cys Ile Glu Ile
465                 470                 475                 480

Pro Leu Ala Gly Met Lys Arg Ala Asn Ala Val Glu Thr Asn Glu Asn
                485                 490                 495

Lys Asn Met Glu Val Ile Ser Thr Glu Met Leu Glu Ser Gly Glu Gly
            500                 505                 510
```

```
Val Tyr Val Leu Leu Ser Gly Asn Ser Ile Val Ser Val Arg Leu Glu
        515                 520                 525
His His His His His His
    530
```

METHOD FOR THE PRODUCTION OF XYLOBIOSE AND OTHER DEFINED XYLOOLIGOSACCHARIDES

CROSS-REFERENCE TO RELATED APPLICATIONS

This patent application claims the benefit of priority of United States Provisional Patent Application No. 62/898,077, filed Sep. 10, 2019, which is incorporated herein by reference in its entirety.

STATEMENT REGARDING FEDERALLY SPONSORED RESEARCH

This invention is owned by and was made with government support from the USDA Forest Service. The government has certain rights in the invention.

SEQUENCE LISTING

A Sequence Listing accompanies this application and is submitted as an ASCII text file of the sequence listing named "920233 00029 ST25" which is 88.2 KB in size and was created on Aug. 28, 2020. The sequence listing is electronically submitted via EFS-Web with the application and is incorporated herein by reference in its entirety.

BACKGROUND OF THE INVENTION

Plant biomass represents a plentiful source of carbohydrates that can be utilized in numerous industries, including in bioconversions by organisms (e.g., bacteria and yeast) or directly with enzymes, food manufacture (i.e., to improve food processing characteristics, food characteristics, and/or nutritive value), farm animal nutrition and welfare, agricultural processes, human health, and pharmaceutical industries. The carbohydrates contained within plant biomass could generate a plentiful, economically competitive feedstock for fermentation into chemicals, plastics, and fuels (e.g., ethanol). However, the enormous potential of these sugars is currently under-utilized as they are locked in complex polymers that are not readily accessible for fermentation. These complex polymers are often referred to collectively as lignocellulose. Accordingly, there remains an unmet need in the art for improved methods that efficiently generate useful degradation products, such as xylobiose and structurally defined xylo-oligosaccharides from lignocellulosic biomass.

SUMMARY

The present invention provides compositions for the production of xylobiose and defined xylo-oligosaccharides. The compositions comprise: (a) an isolated appendage dependent endoxylanase [such as, for example and preferably, an isolated canonical glycoside hydrolase family 30 subfamily 8 (GH30-8) enzyme or other appendage dependent endoxylanase such as, for example, arabinoxylanase]; and (b) an isolated xylobiohydrolase comprising an amino acid sequence with at least 90% identity to a sequence selected from the group consisting of SEQ ID NO:1-13, or a portion thereof with xylobiohydrolase activity.

In another aspect, the present invention provides methods for producing xylobiose. The methods comprise contacting a lignocellulosic biomass material, an enriched xylan fraction thereof, or an extracted, purified xylan material with: (a) an isolated appendage dependent endoxylanase [such as, for example and preferably, an isolated canonical GH30-8 enzyme or other appendage dependent endoxylanase such as, for example, arabinoxylanase]; and (b) an isolated xylobiohydrolase comprising an amino acid sequence with at least 90% identity to a sequence selected from the group consisting of SEQ ID NO:1-13 or a portion thereof with xylobiohydrolase activity; thereby producing a product mixture comprising xylobiose and defined aldouronates.

In yet another aspect, the present invention also provides kits for producing xylobiose. The kits comprise (a) an isolated appendage dependent endoxylanase [such as, for example and preferably, an isolated canonical GH30-8 enzyme or other appendage dependent endoxylanase such as, for example, arabinoxylanase]; and (b) an isolated xylobiohydrolase comprising an amino acid sequence with at least 90% identity to a sequence selected from the group consisting of SEQ ID NO:1-13 or a portion thereof with xylobiohydrolase activity.

These and still other advantages of the invention will be apparent from the detailed description and drawings. What follows is merely a description of some preferred embodiments of the present invention. To assess the full scope of the invention the claims should be looked to as these preferred embodiments are not intended to be the only embodiments within the scope of the claims.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The patent or patent application file contains at least one drawing in color. Copies of this patent or patent application publication with color drawings will be provided by the Office upon requests and payment of the necessary fee.

The present invention will be better understood and features, aspects and advantages other than those set forth above will become apparent when consideration is given to the following detailed description thereof.

DETAILED DESCRIPTION

Figure 1:
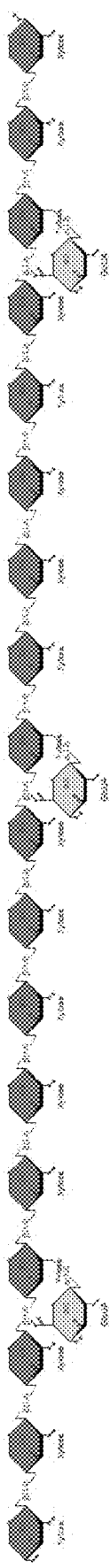
FIG. 1 shows a schematic of model alkaline-extracted hardwood glucuronoxylan.

The present invention provides a novel two-enzyme system by which xylans, such as those found in lignocellulosic biomass material, an enriched xylan fraction thereof, or an extracted, purified xylan material, can be converted into xylobiose and other useful defined oligosaccharide products.

Within lignocellulosic biomass, cellulose microfibrils are embedded in a polysaccharide matrix formed of hemicelluloses such as xylan, (galacto)glucomannan, and xyloglucan. These hemicelluloses may be associated with other lower abundance biomass polysaccharides, such as arabinans, and pectins, depending upon the plant and tissue source. The polysaccharide matrix is also typically surrounded and cross-linked with polyphenolic lignins. The tight interactions that exist between cellulose, hemicellulose, and lignin make it very difficult and expensive to break down this recalcitrant matrix of biomass to yield useful mixtures of oligosaccharides or fermentable simple sugars.

The term "xylan" refers to a class of hemicelluloses that includes glucuronoxylan, acetylglucuronoxylan, acetylarabinoglucuronoxylan, glucuronoarabinoxylan and arabinoxylan. Xylans are polysaccharides made up of β-1,4-linked xylose (a pentose sugar) residues with side branches of α-L-arabinofuranose and α-D-glucuronic acids. Xylans from different plant sources have different chemical characteristics, such as chain length and sugar or non-sugar substitutions. The nature of the substitutions along the xylan chain distinguishes the various types of xylan. For example, depending on the biomass source, a xylan chain may be substituted with O-2 or O-3 linked acetyl groups, α-1,2 and/or α-1,3 linked L-arabinofuranose (Aran, α-1,2 linked D-glucuronic acid or primarily its 4-O-methyl derivative (GA).

The primary xylan found in hardwood and crop residues is a glucuronoxylan (GX), which includes a chain of β-1, 4-linked xylose residues randomly substituted with α-1,2-linked glucuronic acid (GA) residues at a frequency as high as one GA for every six xyloses. Within hardwood lignocellulose, xylan is an acetylglucuronoxylan having a high degree at the O-2 and/or O-3 acetyl substitution. Commercial extraction of these polysaccharides is typically done under alkaline conditions, which deacetylates the xylan. Other lower-yielding extraction procedures must be used to obtain an acetylglucuronoxylan polysaccharide. In softwood, the primary xylan is glucuronoarabinoxylan, which has periodic GA substitutions and α-1,2-linked arabinofuranose substitution primarily on the O-3 hydroxyl positions of xylose. Xylans derived from grasses are seemingly more complex, including primarily of an arabinoglucuronoxylan containing also acetyl substitution. Xylans from sources such as grain endosperm (e.g., wheat and rye) typically include arabinoxylans, which lack GA substitutions, but are heavily substituted with Araf. For these grain arabinoxylans, the current understanding is that single Araf substitutions are linked through the O-3 hydroxyl and O-2 linked Araf substitutions are only observed on a xylose already substituted O-3 making this xylan type the only known to contain double Araf substitutions on a single xylose. Commercially prepared hardwood glucuronoxylan and cereal endosperm arabinoxylan are the only xylan forms that are readily available for routine research purposes. Other xylan forms may be isolated through laboratory methods or protocols with limited success and/or yield.

Figure 4:
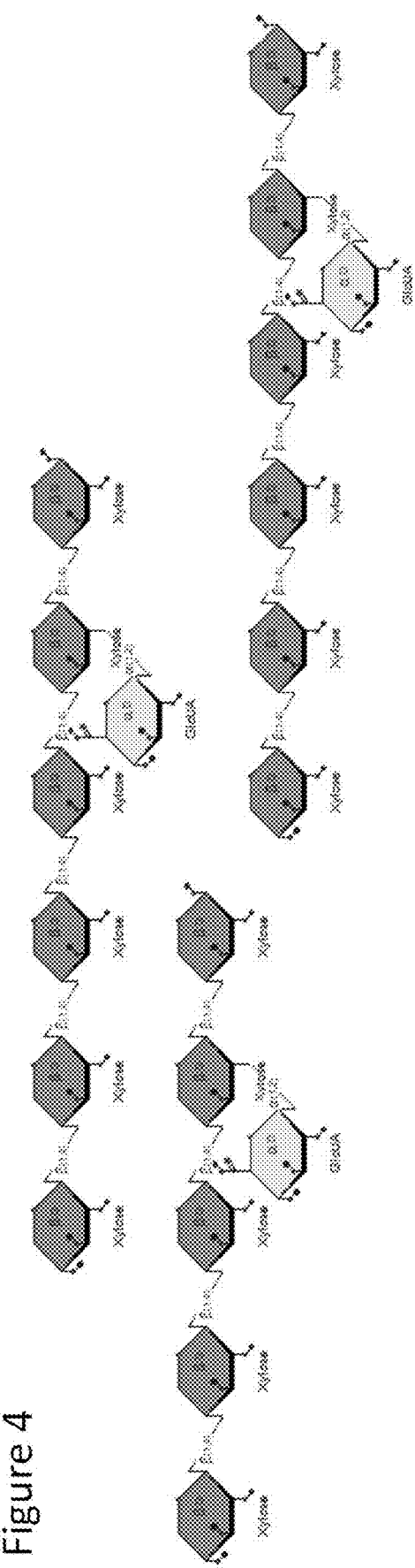
FIG. 4 shows a schematic of an exemplary product of GH30-8 glucuronoxylan xylanohydrolase hydrolysis.

Endoxylanases are enzymes that hydrolyze internal β-1, 4-xylosidic linkages in xylans, thereby producing smaller xylo-oligomers. Glycoside hydrolase family 30 subfamily 8 (GH30-8) enzymes are endoxylanases that hydrolyze glucuronoxylan into a mixed population of aldouronates, which span a broad size range and each contain a single GA substitution on the xylose penultimate to the reducing terminus (FIG. 4). The present inventors have discovered a novel class of xylobiohydrolases, related to the enzyme HcXbh30A (also known as Clocl_1795) found in *Hungateiclostridium clariflavum*, that can be used to cleave xylobiose from the non-reducing terminus of these aldouronates (FIG.

Figure 6:
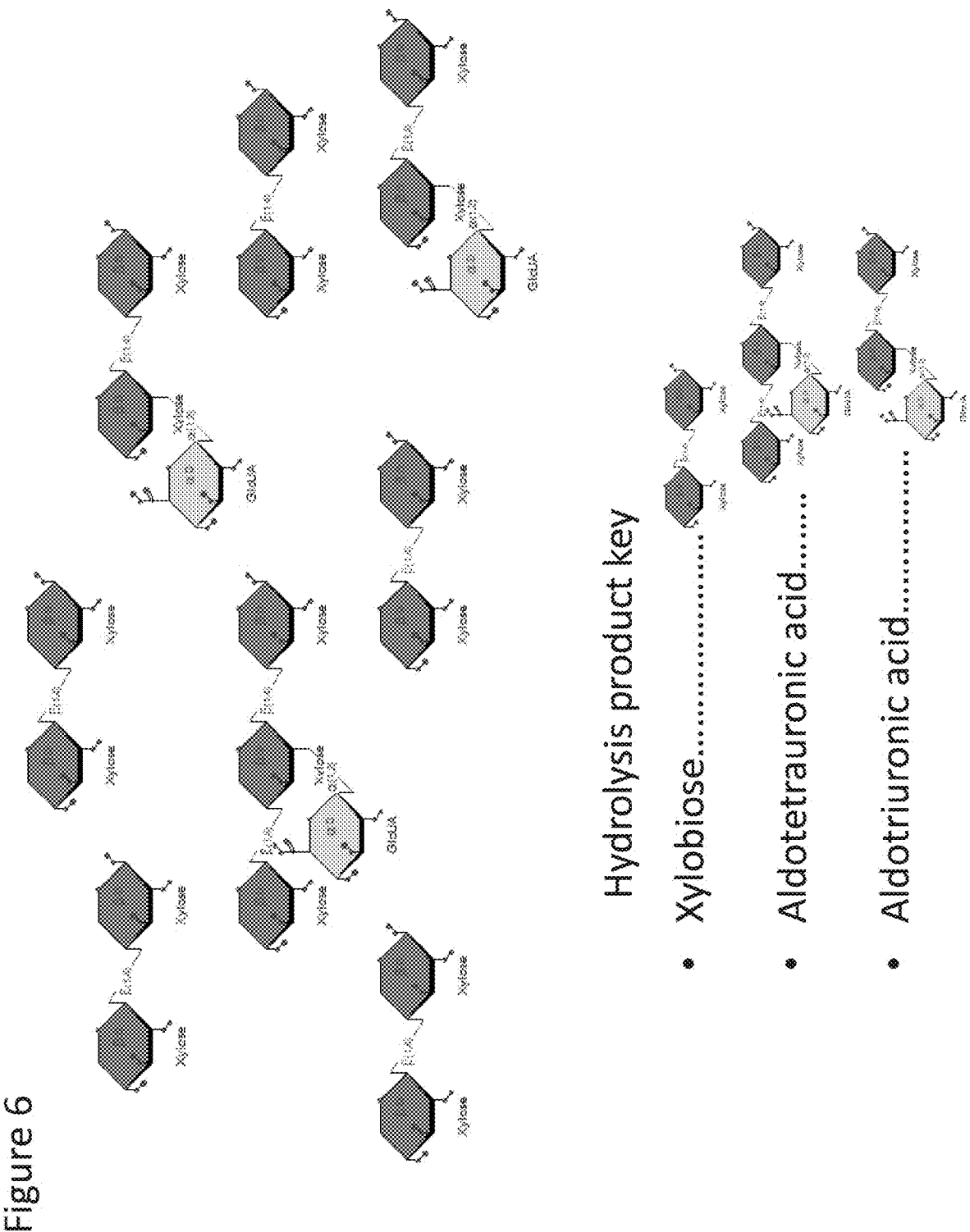
FIG. 6 shows a schematic of the products produced by HcXbh30A hydrolysis of an aldouronate mixture generated by glucuronoxylan xylanohydrolase.

5), thereby generating xylobiose and a defined mixture of aldotriuronic acid and aldotetrauronic acid (FIG. 6). Xylobiose is an industrially useful disaccharide that comprises two xylose monomers linked by a β-1,4-bond and these aldouronates are also of high value in industry. Defined oligosaccharides such as aldotriuronic and aldotetrauronic acid are showing emerging value in feed amendment and neutraceutical applications.

Based on this discovery, the inventors have developed a two-enzyme system in which these endoxylanase and xylobiohydrolase activities are combined to produce specific oligosaccharide products from lignocellulosic biomass [using appendage dependent endoxylanase of which canonical glucuronoxylan xylanohydrolase-1,4-endoxylanase (e.g., GH30-8) and arabinoxylanase have been at least established as workable with an xylobiohydrolase comprising an amino acid sequence with at least 90% identity to a sequence selected from the group consisting of SEQ ID NO:1-13 or a portion thereof with xylobiohydrolase activity]. One of the primary advantages of this two-enzyme system is that it produces a simple mixture of products (e.g., the sugar xylobiose and a mixture of two defined aldouronates) that are easily separated. Most other known xylobiohydrolases have transglycosylation activities that result in the production of a variety of products or show a primary or secondary endoxylanase function. An enzyme demonstrating multiple functions would be expected to have low substrate affinity (a high Michaelis constant, KM) and by extension poor performance. Similarly, the use of other endoxylanases that are less specific than the GA-dependent GH30-8 enzymes, for example, will generate a broader variety of products. The use of two separate enzymes with high functional specificity offers additional advantages in efficiency and reaction control as the two separate activities may be uncoupled and therefore manipulated and used in addition with other glycoside hydrolases for the purpose of generating additional novel substituted xylooligosaccharides.

Compositions:

The present invention provides compositions for the production of xylobiose. The compositions comprise: (a) an isolated canonical glycoside hydrolase family 30 subfamily 8 (GH30-8) enzyme or an alternative appendage dependent endoxylanase activity; and (b) an isolated xylobiohydrolase comprising an amino acid sequence with at least 90% identity to a sequence selected from the group consisting of SEQ ID NO:1-13, or a portion thereof with xylobiohydrolase activity.

In some embodiments, the compositions further comprise (c) a lignocellulosic biomass material, an enriched xylan fraction thereof, or an extracted, purified xylan material. As used herein the terms "lignocellulosic biomass" or "biomass" refer to materials containing cellulose and/or hemicellulose. Generally, these materials also contain pectin, lignin, protein, carbohydrates, and ash. Lignocellulose is the woody material found primarily in plant secondary cell walls that gives plants their rigidity and structure, and is found, for example, in the trunk, stems, leaves, hulls, husks, and cobs of plants or leaves, branches, and wood of trees.

The enzyme compositions are suitably in the form of a product of manufacture, such as a formulation, and can take the physical form of a liquid or a solid. In addition to the essential enzyme components (see section titled "Enzymes" below), the compositions may further comprise polysaccharides (e.g., carboxymethylcellulose, additional proteins (e.g., bovine serum albumin), buffers, stabilizers, or additives such as sugars (e.g., maltose, glycerol), sugar alcohols (e.g., sorbitol), detergents, thickeners, and cryoprotectants (e.g., glycerol, propylene glycol, polyethylene glycol).

Input Material:

Suitable sources of lignocellulosic biomass for use with the compositions and methods of present invention include, without limitation, agricultural biomass, commercial organics, construction and demolition debris, municipal solid waste, waste paper and yard waste. Common forms of biomass include trees, shrubs, grasses, wheat, wheat straw, sugar cane bagasse, sugar beet, soybean, corn, cornhusks, corn kernels, corn cob and byproducts from milling of grains. The biomass can also be, but is not limited to, herbaceous material, agricultural residues, forestry residues, pulp, and paper mill residues. "Agricultural biomass" includes branches, bushes, canes, corn and corn husks, energy crops, algae, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, peat moss, mushroom compost and hard and soft woods. In addition, agricultural biomass includes organic waste materials generated from agricultural processes including farming and forestry activities, specifically including forestry wood waste. In certain embodiments, the lignocellulosic biomass material is derived from hardwood, softwood, or grass.

In certain embodiments, the lignocellulosic biomass material comprises glucuronoxylans, acetylglucuronoxylans, glucuronoarabinoxylans, or arabinoglucuronoxylans. Glucuronoxylans are linear polymers comprising a β-1,4-linked polyxylose chain that are randomly substituted with α-1,2-linked glucuronic acid (GA) appendages. These xylan main chain appendages are also often referred to as xylan chain decorations, side chains, or substitutions (FIG. 1). Industrial production of commercial grade glucuronoxylans include an alkaline extraction of xylan polysaccharides from hardwood, which deacetylates the xylans (i.e., remove esterified O-2 and O-3 acetyl groups), leaving only the α-1,2-GA moieties.

Figure 2:
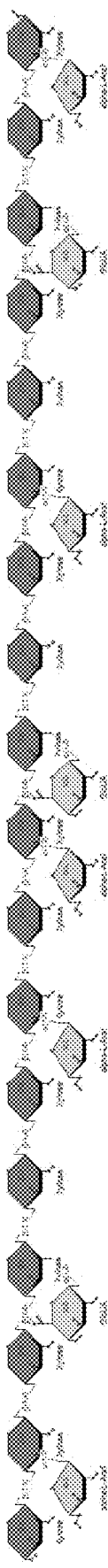
FIG. 2 shows a schematic of alkaline-extracted softwood or grass glucuronoxylan.

In contrast, glucuronoarabinoxylans or arabinoglucuronoxylans may be prepared by alkaline extraction of delignified softwood or grass biomass (FIG. 2). Unlike hardwood xylans, softwood xylans are not acetylated, but include periodic substitutions of GA and α-1,2 or α-1,3-arabinofuranose moieties. Glucuronoarabinoxylans may be used directly as input material in the present methods. In these embodiments, while less xylobiose will ultimately be produced, the methods will generate unique arabinofuranose-substituted aldouronates. These arabinofuranose-substituted aldouronates may be useful, for example, as pharmaceuticals, nutraceuticals, or for inclusion in foods for targeted modulation of the human gut microbiome. Alternatively, for maximum yield of xylobiose, arabinose may be removed prior to treatment. Removal of arabinose may be accomplished by applying mild acid conditions or treating with an appropriate arabinofuranosidase enzyme. In these embodiments, the extracted arabinose may be marketable as a useful byproduct (e.g., for use as a sweetener, nutraceutical, or pharmacologically active sugar, or as a composition produced by bioconversion using a microbial biocatalyst or enzyme (Lim et al., 2016). Optionally, a rinsing step may be included to obtain high purity arabinose prior to digestion with the two-enzyme system.

Enzymes:

The compositions, methods, and kits of the present inventions rely on at least two specific enzyme activities, i.e., canonical GH30-8 endoxylanase activity or an alternative appendage dependent endoxylanase of defined substitution specificity and xylobiohydrolase activity, which are provided by isolated enzymes.

By "isolated enzyme", we mean a polypeptide that has been removed from its native host organism. The enzymes used with the present invention may be isolated from a naturally occurring source or may be recombinantly expressed in a host organism or host cell and purified. In some cases, the enzymes may be purified away from other cellular proteins and components. However, it is contemplated that the enzymes can also be used as a component of a crude cellular extract. Protein expression and purification methods are well known in the art (see, e.g., *Nat Methods*. (2008) 5(2): 135-146).

The term "xylanase" (and more specifically, an "endoxylanase" as used and described herein) refers to an enzyme that digests the linear polysaccharide xylan. These enzymes, which allow organisms to degrade plant matter into usable nutrients, are produced by a wide array of species, including fungi, bacteria, yeast, marine algae, protozoans, snails, crustaceans, insect, and plants. The xylanases used with the present invention are classified as glycoside hydrolase family 30 subfamily 8 (GH30-8) enzymes, a well-characterized group of endoxylanases that strictly hydrolyze glucuronoxylan or other xylan types which contain glucuronic acid appendages. As used herein, a "canonical GH30-8 enzyme" refers to any GH30-8 enzyme that has "appendage-dependent" xylanase activity. Specifically, canonical GH30-8 enzymes cleave the β-1,4-xylosidic linkage of xylan upon recognition of the α-1,2-linked 4-O-methylglucuronic acid (glucuronic acid, GA) side chain appendage. Thus, these enzymes are referred to as glucuronoxylan xylanohydrolases. (Note: A list of synonyms, some of them descriptively inaccurate, can be found in the Gene Ontology Database) (www.ebi.ac.uk). Cleavage of the xylan chain by these enzymes occurs toward the polysaccharide reducing terminus relative to the target glucuronic acid, such that the GA appendage is positioned penultimate to the new reducing terminus. Limit hydrolysis of glucuronoxylan by these "GA-dependent" xylanases primarily results in a distribution of aldouronates in which each contains a single GA appendage substituted on the xylose penultimate to the reducing terminal of the resulting aldouronate (Nishitani and Nevins, 1991; St John et al., 2006a; Vrganska et al., 2007; St John et al., 2011; Urbanikova et al., 2011). These canonical, GA-dependent GH30-8 enzymes are contrasted to a functionally distinct subset of "GA-independent" GH30-8 xylanases that do not require the 0-2 linked GA for cleavage, and thus exhibit a relaxed (or expanded range of) substrate specificity (see U.S. Pat. No. 10,041,136; St John et al., 2014; St John et al., 2018).

Any canonical GH30-8 enzyme or portion thereof with xylanase activity may be used with the present invention as well as potentially other appendage dependent endoxylanases, which are preferably functionally-specific. As used herein, the term "a portion thereof" is used to describe a fragment of an enzyme that retains the canonical enzymatic activity ascribed to the full-length enzyme. Suitably, the fragments of GH30-8 xylanase used with the present invention comprise the core catalytic domain of these enzymes, which includes a $(\beta/\alpha)_8$ TIM barrel fused to a side β-structure composed of 9-antiparallel beta-strands, previously referred to as a $(\beta/\alpha)_8+\beta$ structure (St John et al., 2010). For example, the fragments may comprise amino acid residues 33-422 of SEQ ID NO:15 (UniProt: Q45070). In some embodiments, the GH30-8 enzyme used with the present invention has at least 90% identity to a sequence selected from the group consisting of SEQ ID NO:14-18, which include canonical GH30-8 enzymes found in the gram positive bacteria *Clostridium thermocellum* (UniProt: A3DJS9; SEQ ID NO:14), *Bacillus subtilis* (UniProt: Q45070; SEQ ID NO:15), and *Clostridium acetobutylicum* (UniProt: Q97TI3; SEQ ID NO:16), and in the Gram negative bacteria *Dickeya dadantii* (UniProt: Q46961; SEQ ID NO:17), *Xanthomonas campestris* (UniProt: GOCEN3; SEQ ID NO:18), and *Bacteroides cellulosilyticus* (NCBI Reference Sequence: WP_029428491.1; SEQ ID NO:19). In some embodiments, the compositions comprise 2 or more, 3 or more, 4 or more, or even 5 or more GH30-8 xylanases to promote efficient degradation of xylan.

In some embodiments, the full amino acid sequence of the xylanase has been modified. The full-length xylanase amino acid sequence encodes a leader peptide that is not required for xylanase function. Accordingly, the inventors have engineered variants of these enzymes in which an N-terminal leader (e.g., amino acids 1-18, although note this is enzyme variable) and/or a C-terminal non-catalytic domain have been removed and in which a C-terminal HIS tag has been added (SEQ ID NO:20). The presents or absence of N-terminal secretion leader sequences or N or C-terminal non-catalytic domains may vary based on the intended expression/purification strategies which may be employed for the production of these enzymes and based also of complimentary functional attributes.

The term "xylobiohydrolase" refers to an enzyme that cleaves the disaccharide xylobiose from the end of a xylan chain. Herein, a xylobiohydrolase family is newly identified, is phylogenetically distinct from known xylobiohydrolases and unlike previously characterized xylobiohydrolases is shown to have functional specificity, with no evidence of secondary hydrolytic activity. Suitable xylobiohydrolases for use with the present invention include several closely related homologs found in *Hungateiclostridium clariflavum* (UniProt: G8LU16; SEQ ID NO:1), *Pseudobacteroides cellulosolvens* (UniProt: A0A0L6JSW0; SEQ ID NO:2), *Ruminiclostridium cellobioparum* (UniProt: S0FYK9; SEQ ID NO:3), *Ruminiclostridium hungatei* (UniProt: A0A1V4SJD0; SEQ ID NO:4), *Ruminiclostridium papyrosolvens* (UniProt: U4R474; SEQ ID NO:5), *Ruminiclostridium cellulolyticum* (UniProt: B817A6; SEQ ID NO:6), *Clostridium* sp. BNL1100 (UniProt: H2JJG2; SEQ ID NO:7), *Ruminiclostridium papyrosolvens* (UniProt: F1TES6; SEQ ID NO:8), *Ruminiclostridium sufflavum* (UniProt: AOA318YBK9; SEQ ID NO:9), and *Ruminiclostridium* sp. MA18 (UniProt: A0A4U7JJW1; SEQ ID NO:10). Notably, the inventors have confirmed the xylobiohydrolase activity of the enzyme of SEQ ID NO:1, which is referred to herein as HcXbh30A (also known as Clocl_1795) and of the enzyme of SEQ ID NO:2. The additional homologs provided herein share greater than 68% sequence identity with HcXbh30A based on an alignment of their full amino acid sequence, and share greater than 73% sequence identity based on an alignment of only the primary region of the catalytic domain. All of these enzymes establish a single Glade in phylogenetic analysis.

Notably, in some embodiments, the xylobiohydrolase comprises only a portion of one of the disclosed sequences that has xylobiohydrolase activity. Suitably, the fragments of xylobiohydrolase enzymes used with the present invention comprise the core catalytic domain of these enzymes, which include a $(\beta/\alpha)_8+\beta$ structure. For example, the fragments may comprise amino acid residues 29-460 of SEQ ID NO:1 (UniProt: G8LU16). Thus, the portion of the xylobiohydrolase used with the present invention suitably includes the predicted catalytic domain of the enzyme. In some embodiments, the compositions comprise 2 or more, 3 or more, 4 or more, or even 5 or more xylobiohydrolases disclosed herein to promote efficient degradation of xylan.

In some embodiments, the full amino acid sequence of the xylobiohydrolase has been modified. The full-length xylobiohydrolase amino acid sequence encodes a signal peptide that is required for secretion when expressed in the enzyme's native biological source organism and a dockerin domain that allows the native enzyme to bind to the extracellular cellulosome organelle. Neither of these domains are needed for xylobiohydrolase function. Accordingly, the inventors have engineered variants of these enzymes in which an N-terminal signal peptide (amino acids 1-28) has been removed and in which a C-terminal HIS tag has been added (SEQ ID NO:11-13). The inventors have also engineered variants in which the predicted dockerin domain (amino acids 464-535) has been removed (SEQ ID NO:12). The presents or absence of N-terminal secretion leader sequences or N or C-terminal non-catalytic domains may vary based on the intended expression/purification strategies which may be employed for the production of these enzymes and based also of complimentary functional attributes.

In some embodiments, additional enzymes derived from other microorganisms, plants, or organisms are included in the compositions, methods, and kits disclosed herein. Suitable enzymes for use with the present invention include, without limitation, enzymes having xylosidase activity, cellobiohydrolase activity, β-glucosidase activity, cellulase activity, β-xylosidase activity, arabinofuranosidase activity, arabinoxylanase activity, lytic polysaccharide monooxygenase activity, lyase activity, α-glucosidase activity, α-glucuronidase activity, β-glucuronidase activity, β-1,4-xylosidase, β-1,3-xylosidase activity, β-1,3-endoxylanase activity, β-1,4-reducing-end xylosidase (REX) activity, β-1,4-endoxylanase activity, α-xylosidase activity, fucosidase activity, endomannanase activity, α-mannosidase activity, β-mannosidase activity, galactosidase activity, galactanase activity, mixed linkage β-endoglucanase activity, β-1,4-endoglucanase activity, carbohydrate lyase activity, β-1,3-endogalactanase activity, β-1,6-endogalactanase activity, β-1,4-endogalactanase activity, β-1,4-endomannanase activity, or endoglucanase activity.

The arabinoxylanase functions in a manner analogous to the canonical GH30-8 glucuronic acid appendage dependent endoxylanases except that this enzyme requires the recognition of an α-1,3-linked arabinofuranose appendage for endoxylanase activity to occur. Further, the xylan cleavage site is different from the GH30-8 enzymes in that the arabinofuranose substituted xylose is not penultimate from the reducing terminus, but rather is the new reducing terminal xylose. Other appendage dependent endoxylanases also exist but function with less strict functional requirements.

The additional enzymes may be used, for example, to increase the yield of xylobiose or to prepare novel oligosaccharides. For example, a softwood arabinoglucuronoxylan may be pretreated with an arabinofuranosidase to remove arabinofuranose substitutions prior-to or together-with the application of the xylobiose enzyme system. In a second example, a similar xylan as above could be treated with the xylobiohydrolase enzyme system to yield a novel population of arabinofuranose-substituted aldouronates. Following deactivation of the xylobiohydrolase activity, these novel arabinofuranose-substituted aldouronates could be subsequently treated with an arabinofuranosidase or an arabinoxylanase to yield additional novel products of defined structure. Thus, in some embodiments, the additional enzyme is selected from arabinofuranosidase or arabinoxylanase. As a third example, the same population of arabinofuranose substituted aldouronates could be processed with either a β-xylosidase or α-glucuronidase to generate another set of novel oligoxylosides with variable α-glucuronic acid (or it 4-O-methyl derivative) and/or arabinofuranose substitutions of defined structure. Of the two demonstrated appendage dependent endoxylanase activities (i.e., GH30-8 and arabinoxylanase), the one not used for the initial xylobiohydrolase processing may be used as a secondary enzyme in the generation of oligosaccharides similar to the use of the β-xylosidase, α-glucuronidase, and arabinofuranosidases.

From above it can be seen that, not only can xylobiose be a product, but xylobiose and a small simple set of xylo-oligosaccharides that are readily purifiable, the specific composition of which is determined by the primary enzyme, for which GH30-8 is the demonstrated model, but could include instead, for example, arabinoxylanase.

For use in the present invention, the enzymes may be provided as nucleic acid constructs that encode the enzymes. The xylanase and xylobiohydrolase enzymes may be provided in the form of two separate constructs, each encoding one enzyme. Alternatively, the xylanase and xylobiohydrolase enzymes may be encoded in a single dual-enzyme construct. The dual-enzyme construct may encode the enzymes in separate transcriptional units or as a single fusion protein in which the enzymes are connected by a linker peptide.

In some embodiments, the nucleic acid construct(s) encoding the enzymes are cloned into an expression vector. As used herein, an "expression vector" is DNA comprising a gene operatively linked to a regulatory element (e.g., a promoter). The expression vector may contain one or more such gene/regulatory element combinations. The expression vector may also include additional sequences, such as a signal sequence or a tag, that modify the protein produced by the transgene. The expression vector may also include a genetic marker that allows transformed cells containing the vector to be recovered by selection.

In some embodiments, the two-enzyme system is expressed in a plant prior harvest, allowing for in situ processing of the plant biomass. This can be achieved by transforming an expression vector encoding the enzymes into a plant cell. Methods for producing transgenic plants are well known in the art. General descriptions of plant expression vectors, reporter genes, and transformation protocols can be found in Gruber, et al., "Vectors for Plant Transformation", in Methods in Plant Molecular Biology & Biotechnology in Glich, et al., (Eds. pp. 89-119, CRC Press, 1993). General methods of culturing plant tissues are provided for example by Maki, et al., "Procedures for Introducing Foreign DNA into Plants" in Methods in Plant Molecular Biology & Biotechnology, Glich, et al., (Eds. pp. 67-88 CRC Press, 1993); and by Phillips, et al., "Cell-Tissue Culture and In-Vitro Manipulation" in Corn & Corn Improvement, 3rd Edition; Sprague, et al., (Eds. pp. 345-387 American Society of Agronomy Inc., 1988). Methods of introducing expression vectors into plant tissue include direct gene transfer methods, such as microprojectile-mediated delivery, DNA injection, and electroporation, as well as the direct infection or co-cultivation of plant cells with *Agrobacterium tumefaciens*, described for example by Horsch et al., Science, 227:1229 (1985). Descriptions of *Agrobacterium* vector systems and methods for *Agrobacterium*-mediated gene transfer are provided by Gruber, et al., supra.

To produce the desired product mixture from a given lignocellulosic input material, the ratio of xylanase, xylobiohydrolase, and any optional additional enzymes used with the present invention may need to be optimized. One of skill in the art can readily identify a suitable ratio of enzymes for a particular application using assays that detect polysaccharide hydrolysis limit products (e.g., high-performance liquid chromatography (HPLC), thin-layer chromatography, gas chromatography, and quantitative mass spectral analysis) or reducing sugars (e.g., the Nelson test).

Advantageously, the present invention should utilize an effective amount of the GH30-8 xylanase, xylobiohydrolase, and any additional enzymes. By "effective amount," we mean an amount that is sufficient to catalyze or aid the digestion or conversion of hemicellulose in lignocellulosic biomass material to a desired xylooligosaccharide composition. In one embodiment, an "effective amount" comprises the amount required to convert polymeric xylan, under ideal conditions, to the limit xylooligosaccharides with depletion of the polymer in a given period of time. For example, the GH30-8 xylanase and/or the xylobiohydrolase can constitute about 0.05 wt. % to greater than 99 wt. % (e.g., about 0.05 wt. % to about 70 wt. %, about 0.1 wt. % to about 60 wt. %, about 1 wt. % to about 50 wt. %, about 10 wt. % to about 40 wt. %, about 20 wt. % to about 30 wt. %, about 2 wt. % to about 45 wt %, about 5 wt. % to about 40 wt. %, about 10 wt. % to about 35 wt. %, about 2 wt. % to about 30 wt. %, about 5 wt. % to about 25 wt. %, about 5 wt. % to about 10 wt. %, about 9 wt. % to about 15 wt. %, about 10 wt. % to about 20 wt. %, etc) of the total proteins in the enzyme compositions disclosed herein. The enzymes may be quantified using standard protein quantification methods, e.g., using UV absorption, a Bradford assay, or a Qubit Protein Assay.

Methods:

The present invention also provides methods for producing xylobiose. The methods comprise contacting a lignocellulosic biomass material, an enriched xylan fraction thereof, or an extracted, purified xylan material with: (a) an isolated appendage-dependent endoxylanase that is preferably functionally-specific such as, for example, an isolated canonical glycoside hydrolase family 30 subfamily 8 (GH30-8) enzyme or arabinoxylanase; and (b) an isolated xylobiohydrolase comprising an amino acid sequence with at least 90% identity to a sequence selected from the group consisting of SEQ ID NO:1-13 or a portion thereof with xylobiohydrolase activity; thereby producing a product mixture comprising xylobiose.

Figure 7:
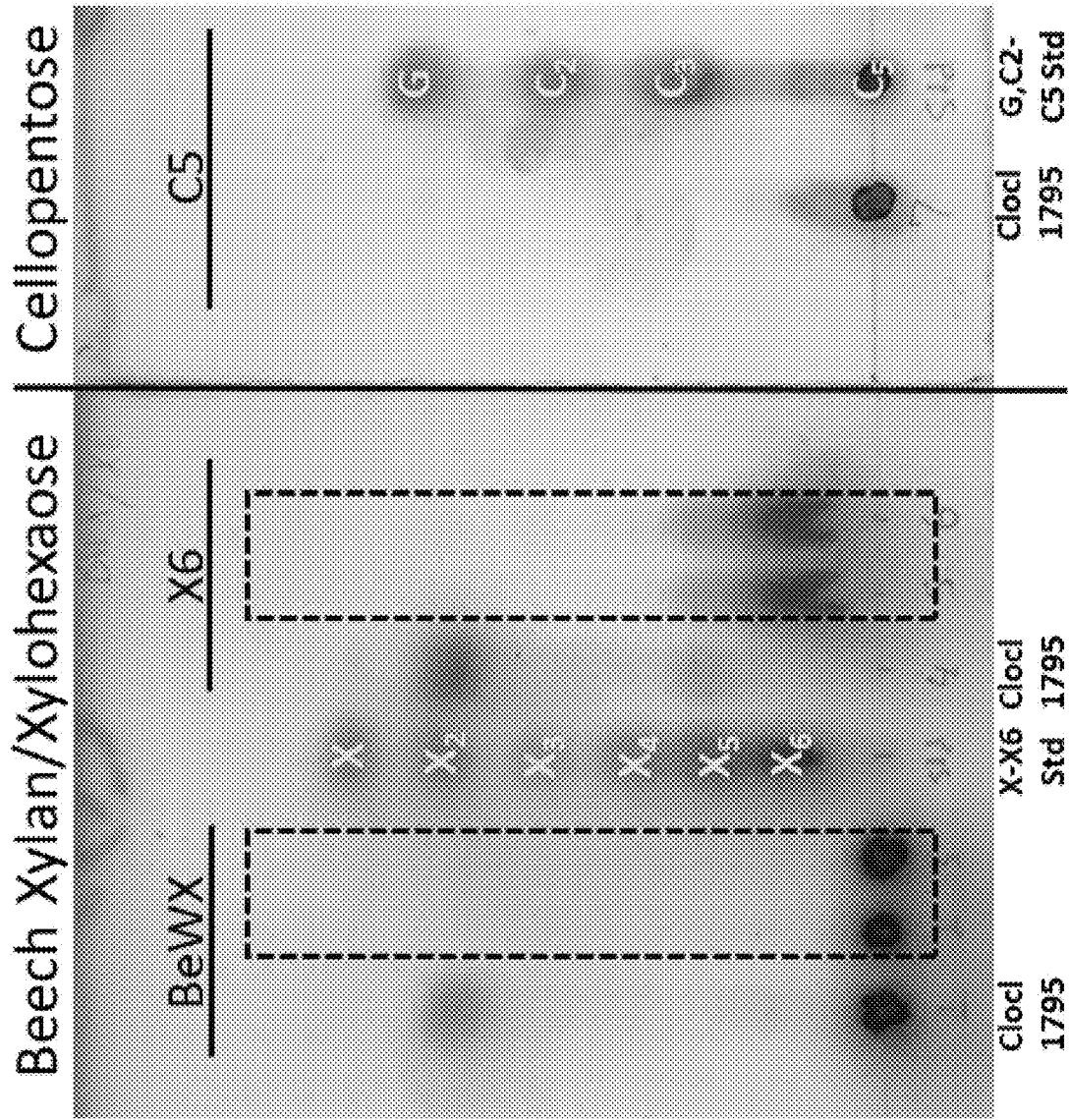
FIG. 7 shows thin-layer chromatography (TLC) results that demonstrate that HcXbh30A has xylobiohydrolase activity. The left panel demonstrates that HcXbh30A specifically releases xylobiose from both a glucuronoxylan (beech xylan, BeWx) and a model xylooligosaccharides (xylohexaose, X6). The right panel demonstrates that HcXbh30A is not able to act as a cellobiohydrolase, indicating that the C6 position of glucose is not accommodated in the HcXbh30A substrate-binding cleft. The dashed-line boxes represent analysis of unrelated enzymes.

The methods of the present invention can be applied in any industry for the reduction of xylans to novel mixtures of xylooligosaccharides or fermentable simple sugars. In some embodiments, the lignocellulosic biomass material comprises deacetylated glucuronoxylans and the methods produce a mixture of specific sugars: xylobiose, aldotriuronic acid, and aldotetrauronic acid (FIG. 6 and FIG. 7). The relative yield of aldotriuronic acid and aldotetrauronic acid depends on the length of the aldouronate hydrolysis products released by the canonical GH30-8 endoxylanase. Even length aldouronates will generate aldotriuronic acid while odd length aldouronates will yield aldotetrauronic acid (FIG. 6). However, any lignocellulosic biomass material may be used as input material in these methods as discussed above in the section titled "Input Materials", and any of the enzymes discussed above in the section titled "Enzymes" may be used in these methods.

In some embodiments, the methods further comprise isolating xylobiose from the product mixture. While the aldouronates produced by the present methods are acidic, the xylobiose has a neutral charge. Thus, xylobiose can be readily purified from the aldouronates using a charge-based separation method. Suitable methods for isolating xylobiose include, without limitation, ion exchange chromatography or high-performance liquid chromatography.

With the two-enzyme system described herein, the initial hydrolysis of the lignocellulosic biomass material, an enriched xylan fraction thereof or an extracted, purified xylan material is performed by the GH30-8 enzyme or other appendage dependent endoxylanase. Thus, in some embodiments, the substrate materials as described above are contacted with the GH30-8 enzyme before it is contacted with the xylobiohydrolase. Alternatively, for simplicity, the GH30-8 enzyme and the xylobiohydrolase may be included in the same reaction.

The GH30-8 xylanases and xylobiohydrolases of the present invention may be applied in conjunction with other additional enzymes, such as arabinofuranosidases, arabinoxylanases, β-xylosidases and α-glucuronidases to affect the final structure of the resulting oligoxyloside products in understood ways. These additional enzymes may be included in the same digestion reaction as the GH30-8 enzyme and/or the xylobiohydrolase, may be used to pre-treat the lignocellulosic biomass material, an enriched xylan fraction thereof or an extracted, purified xylan material prior to digestion with the two-enzyme system, or may be subsequently applied to the products generated by the two-enzyme system. Additional enzymes may be used to enhance the degradation of xylans or to produce complex xylooligosaccharide mixtures, as discussed above in the section titled "Enzymes." Between treatment steps, enzyme inactivation by heat treatment or other means may be required to obtain the desired target oligosaccharide.

The methods may further comprise pretreatment steps that serve to increase the yield of xylobiose. The amount of xylobiose produced depends on the initial degree of substitution of the xylan in the input material. Specifically, when the xylan is less substituted, more xylobiose will be produced, and vice versa. Thus, in some embodiments the methods further comprise extracting glucuronoxylan from hardwood using alkaline extraction prior to enzymatic digestion. In other embodiments, the methods further comprise pretreating glucuronoarabinoxylan or arabinoglucuronoxylan to remove arabinose.

Additionally, the methods may further comprise steps that alter the compositional character of the resulting products, e.g., to generate novel oligosaccharides in addition to xylobiose. For example, alternative xylan extraction procedures may be used to alter characteristics of the xylans in the product mixture.

In the present methods, the enzymes may be added as a dry powder or as a concentrated or diluted aqueous or non-aqueous solution to lignocellulosic biomass material. To achieve the desired digestion products, the enzymes must be incubated with the lignocellulosic biomass material at an appropriate temperature for an appropriate duration. The particular digestion conditions may need to be optimized depending on several factors including, for example, the input material, the specific enzymes that are utilized, the ratio of enzymes utilized, and the desired product mixture. One of skill in the art can readily assess the output generated with a particular set of digestion conditions using assays that detect polysaccharide hydrolysis limit products (e.g., high-performance liquid chromatography (HPLC), thin-layer chromatography, gas chromatography, and quantitative mass spectral analysis) or reducing sugars (e.g., the Nelson test).

Kits:

The present invention also provides kits for producing xylobiose. The kits comprise (a) an isolated appendage dependent endoxylanase (e.g., a canonical GH30-8 enzyme); and (b) an isolated xylobiohydrolase comprising an amino acid sequence with at least 90% identity to a sequence selected from the group consisting of SEQ ID NO:1-13 or a portion thereof with xylobiohydrolase activity.

In some embodiments, the kits further comprise at least one enzyme selected from the group consisting of an arabinofuranosidases, an arabinoxylanase, a β-xylosidase and/or α-glucuronidase.

Applications

The two-enzyme system of the present invention can be used in any lignocellulose-based process, including in research, agricultural, industrial, and commercial settings, as the oligosaccharides, substituted oligosaccharides, and/or monosaccharides produced by this system are useful in many applications. For instance, the two-enzyme system of the present invention may find applications in wood, paper, and pulp treatments; treating fibers and textiles; food processing and supplementation; reducing the mass and volume of substantially untreated solid waste; and in detergent, disinfectant or cleanser compositions. Given that lignocellulosic biomass is a renewable resource, there is a growing interest in using it to make products and fuels, thereby reducing greenhouse gas emissions. There is also interest for use of such enzymes in processing of dough and in the preparation of other foods and beverages.

Xylooligosaccharides have great prebiotic potential. Xylobiose is a substrate for colonic commensal bacteria and its fermentation produces short chain fatty acids, improves gut epithelial health, and regulates metabolic process. For example, supplementation with xylooligosaccharides has been shown promote intestinal health in the elderly (*Nutrition Research* (2007) 27, 756-761). Thus, the two-enzyme system of the present invention may be used in the preparation of prebiotics and food additives. A particular advantange of the two enzyme system here is the ability to utilize other appendage dependent endoxylanases to generate desired alternative xylooligosaccharides for specific prebiotic purposes in addition to the xylobiose product stream.

Additionally, xylooligosaccharides have been shown exhibit anti-inflammatory properties and to provide other health benefits. For example, xylose has been found to confer protection against myocardial injury (*Sci Rep.* (2016) 6, 38728), and there is evidence that glucuronoxylans inhibit the growth and migration of cancer cells (*J. Nat. Prod.* (2007) 70(1):60-66; *Carbohydr Res.* (2014) 393:43-50). Glucuronoxylan derived alduronates have been sulfonated to generate the pharmaceutical pentosan polysulfate (PPS), which has been used successfully in the treatment of painful bladder syndrome (i.e., interstitial cystitis) (Anderson and Perry, 2006) and is under investigation for treatment of other diseases, such as osteoarthritis (Schuchman et al., 2013; Munteanu et al., 2000; Goodrich and Nixon, 2006; McIlwraith et al., 2012; Oehme et al., 2014). Thus, the two-enzyme system of the present invention may also be used in the preparation of therapeutic treatments and nutraceuticals.

Further, digestion with β-xylosidase hydrolyzes xylobiose into xylose, which can be used to produce ethanol and second-generation biofuels such as butanol, furfural, and xylitol. Ethanol offers great promise as a renewable energy source; furfural is used as a flavoring agent in many foods and beverages, as well as in chemical feedstocks, solvents, polymers, and industrial fuels; and xylitol is used as a natural food sweetener, which helps to reduce dental cavities and acts as a sugar substitute for diabetic patients.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description of the novel compounds and methods of the present invention are to be regarded as illustrative in nature and not restrictive.

EXAMPLES

The *Hungateiclostridium clariflavum* glycoside hydrolase family 30 (GH30) protein HcXbh30A (Clod 1795) was first identified in a study of the cellulosome proteomics (Artzi et al., 2015). This study showed that when *H. clariflavum* was cultured on cellulosic substrates, HcXbh30A (Clod 1795) was highly represented within the proteome (Artzi et al., 2015). In one case, it was found to be the second most abundant protein. This finding highlighted the importance of this enzyme in biomass utilization by *H. clariflavum* and distinguished the cellulosome of this bacterium from that of better-studied clostridia species, such as *Clostridium thermocellum*.

Figure 10:
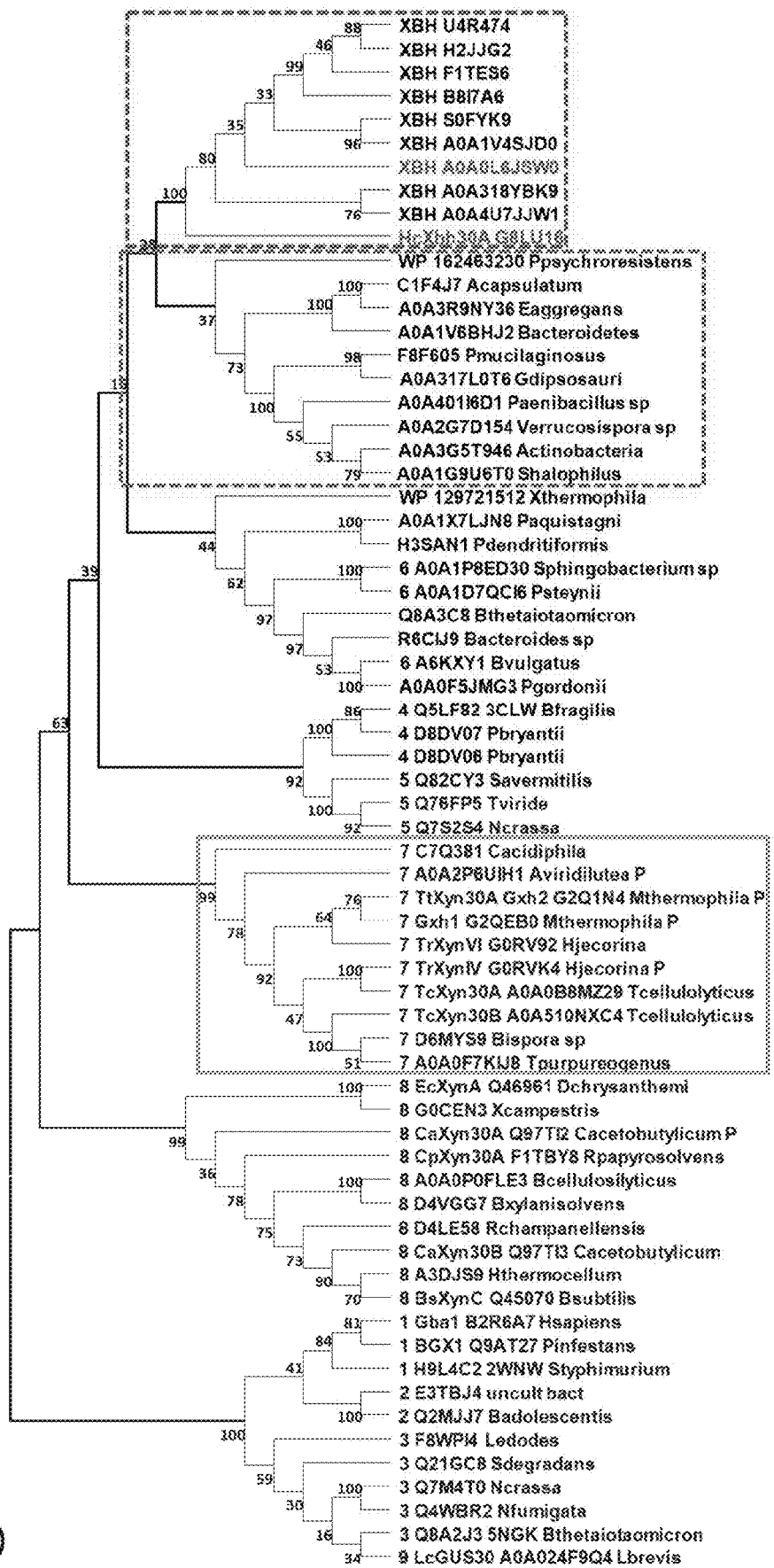
FIG. 10 shows the evolutionary relationships of HcXbh30A. Highlighted in red text are the xylobiohydrolase (XBH) HcXbh30A, which is the functional type enzyme for the associated phylogenetic Glade and the additional enzyme selected for functional verification (XBH A0A0L6JSW0). The grey box includes GH30 subfamily 7 enzymes, which present as a phylogenetic enigma given the relatively tight grouping and large functional diversity in this subfamily. Some GH30-7 enzymes have the reported glucuronoxylanase/XBH multi-function while others have REX activity. The dashed blue box highlights a family that is closely related to the XBH but has not been shown to have XBH function (both the F8F605 Pmucilaginosus and A0A317L0T6 Gdipsosauri enzymes have been tested).

In the following Example, the inventors demonstrate that HcXbh30A is a nonreducing terminal (NRT) specific xylobiohydrolase. The His-tagged form of the predicted catalytic domain has been biochemically characterized. Optimal biophysical parameters were determined and specific activities were measured for several xylooligosaccharide substrates. HcXbh30A strictly cleaves xylobiose from the NRT until it reaches an α-1,2-linked glucuronic acid (GA) decorated xylose if the number of xyloses is even, otherwise a single xylose will remain before the penultimate GA substituted xylose. Unlike another recently reported family of xylobiohydrolases, i.e., GH30 subfamily 7, HcXbh30A produces no other detectable polymeric xylan hydrolysis products. While HcXbh30A is phylogenetically most related to the functionally unassigned GH30 subfamily 6, sequence analysis indicates that HcXbh30A represents a new and distinct GH30 subfamily (FIG. 10). This novel xylobiohydrolase may be useful in any application that relies on the production of xylobiose, including production of prebiotics.

Materials and Methods:

Reagents. All reagents used for the biochemical assays and enzyme studies described herein were of the highest purity. Xylooligosaccharides and cellotetraose were purchased from Megazyme International (Wicklow Ireland). Beech wood xylan and birch wood xylan were purchased from Sigma-Aldrich.

Cloning, Expression and Purification. An expression construct was obtained from Professor Edward Bayer at the Weizmann Institute Rehovot, Israel and used as template to generate alternative protein expression products by PCR. These were cloned into pET28 between the NcoI and XhoI sites. The final expression vector generated for this study included a GH30 catalytic domain with the signal peptide predicted secretion signal sequence replaced with a methionine start codon and a C-terminal linker region and dockerin domain replaced with a His-Tag (SEQ ID NO:12). Protein was expressed using slightly modified auto induction methods originally detailed by Studier (Studier, 2005). Selection was maintained using 50 ug/ml kanamycin and expression proceeded at 18° C. for over 30 hours. Cells were recovered by centrifugation (8,000×g) and collected cell pellets were processed in preparation for immobilized metal affinity chromatography (IMAC), as previously detailed (St John et al., 2018).

Figure 9:
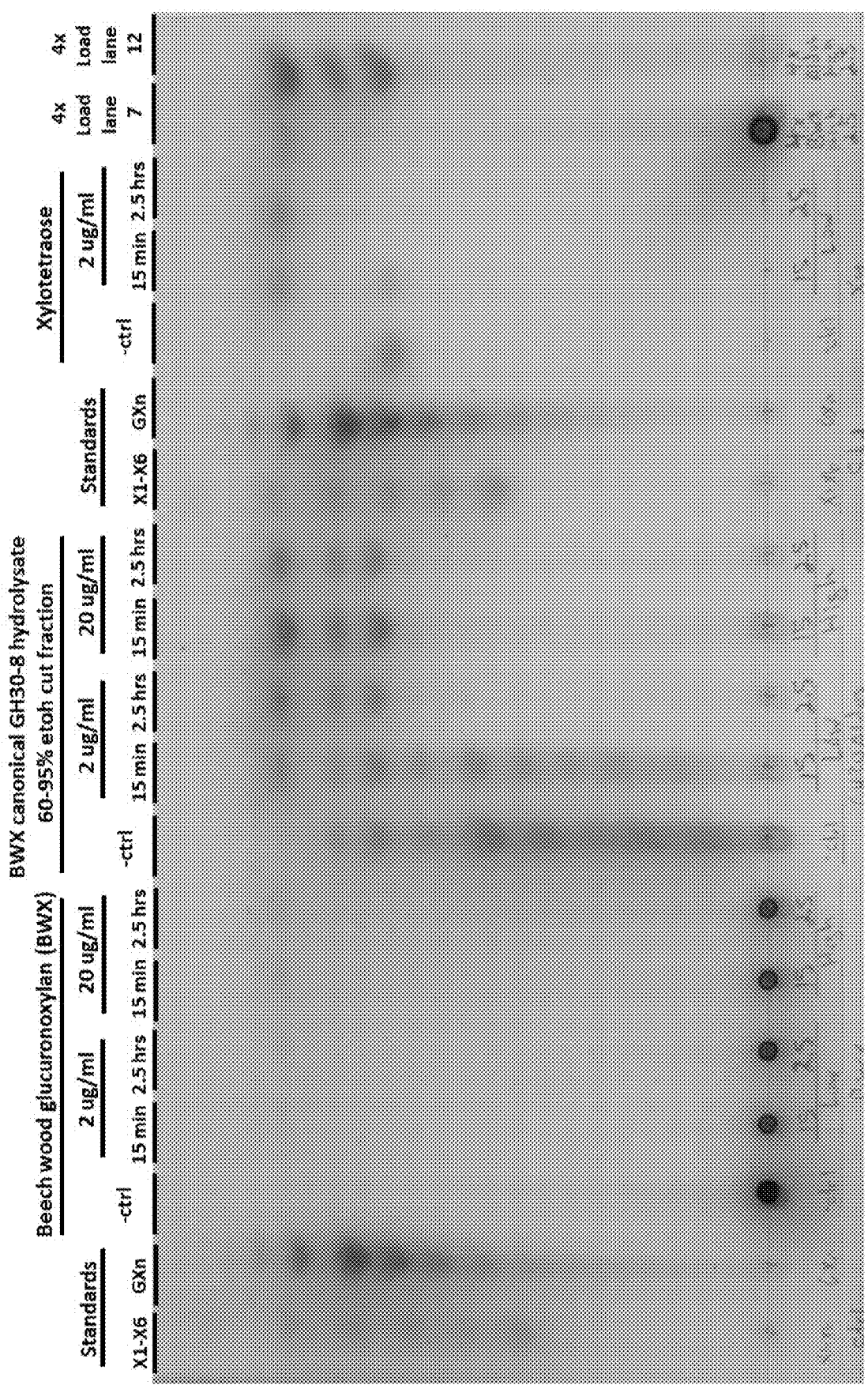
FIG. 9 shows TLC results from a variation of the experiment depicted in FIG. 8. Here, the long reactions were only increased in length by 10× and an alternative TLC mobile phase, consisting of 25:10:5:1:15, ethyl acetate:acetic acid:2-propanol:formic acid:water, was used. This alternative mobile phase more effectively resolves larger xylooligosaccharides and aldouronates, showing a linear distribution of sugars. This would allow for better visualization of any secondary hydrolysis products generated by HcXbh30A.

Biochemical Assays. An initial assessment of HcXbh30A activity was performed using thin layer chromatography according to a previously published method (Bounias, 1980; St John et al., 2006). FIG. 9 used an alternative TLC mobile phase (Biely et al., 2014) to better visualize if secondary unexpected hydrolysis or transglycosylation products were produced following the aggressive enzyme load and reaction time reactions. This mobile phase included ethyl acetate-2-propanol-acetic acid-formic acid-water (25:10:5:1:15, v/v). For small scale TLC reactions sodium acetate was used at 30 mM and BSA was added to enhance HcXbh30A enzyme stability. To optimize the reaction conditions for this enzyme, a custom buffer system including sodium formate, sodium acetate, IVIES (2-[4-morpholino]ethane sulfonic acid), and MOPS (3-[N-morpholino]propane-sulfonic acid) was used to cover the pH range from 2.5-8.0. Single-component buffers of the same concentration were also utilized for comparison. Small volume (i.e., 30 µl), temperature-equilibrated reaction mixtures containing 0.02 mg/ml BSA and 30 mM buffer(s) were prepared. Reactions were initiated by addition of enzyme. Reactions were stopped by addition of an equal reaction volume of 150 mM Tris base pH 8.0 followed by flash freezing in LN2. The reaction mixtures were transferred to a 95° C. water bath for 3-4 minutes, and then transferred to a preheated (>100° C.) Speed-Clave No. 777 (Wilmot Castle Company, Rochester, N.Y.) and incubated at 121° C. for 15 minutes. Samples were subsequently cooled in ice water, vortexed and centrifuged for 5 minutes. The supernatant was removed for direct analysis by HPLC.

Phylogenetic tree construction. The evolutionary history was inferred using the Neighbor-Joining method (Saitou, 1987). The bootstrap consensus tree inferred from 100 replicates is taken to represent the evolutionary history of the taxa analyzed (Felsenstein, 1985). Branches corresponding to partitions reproduced in less than 50% bootstrap replicates are collapsed. The percentage of replicate trees in which the associated taxa clustered together in the bootstrap test (100 replicates) are shown next to the branches (Felsenstein, 1985). The evolutionary distances were computed using the JTT matrix-based method (Jones, 1992) and are in the units of the number of amino acid substitutions per site. The rate variation among sites was modeled with a gamma distribution (shape parameter=1). This analysis involved 66 amino acid sequences. All ambiguous positions were removed for each sequence pair (pairwise deletion option). There were a total of 878 positions in the final dataset. Evolutionary analyses were conducted in MEGA X (Kumar, 2018).

Figure 8:
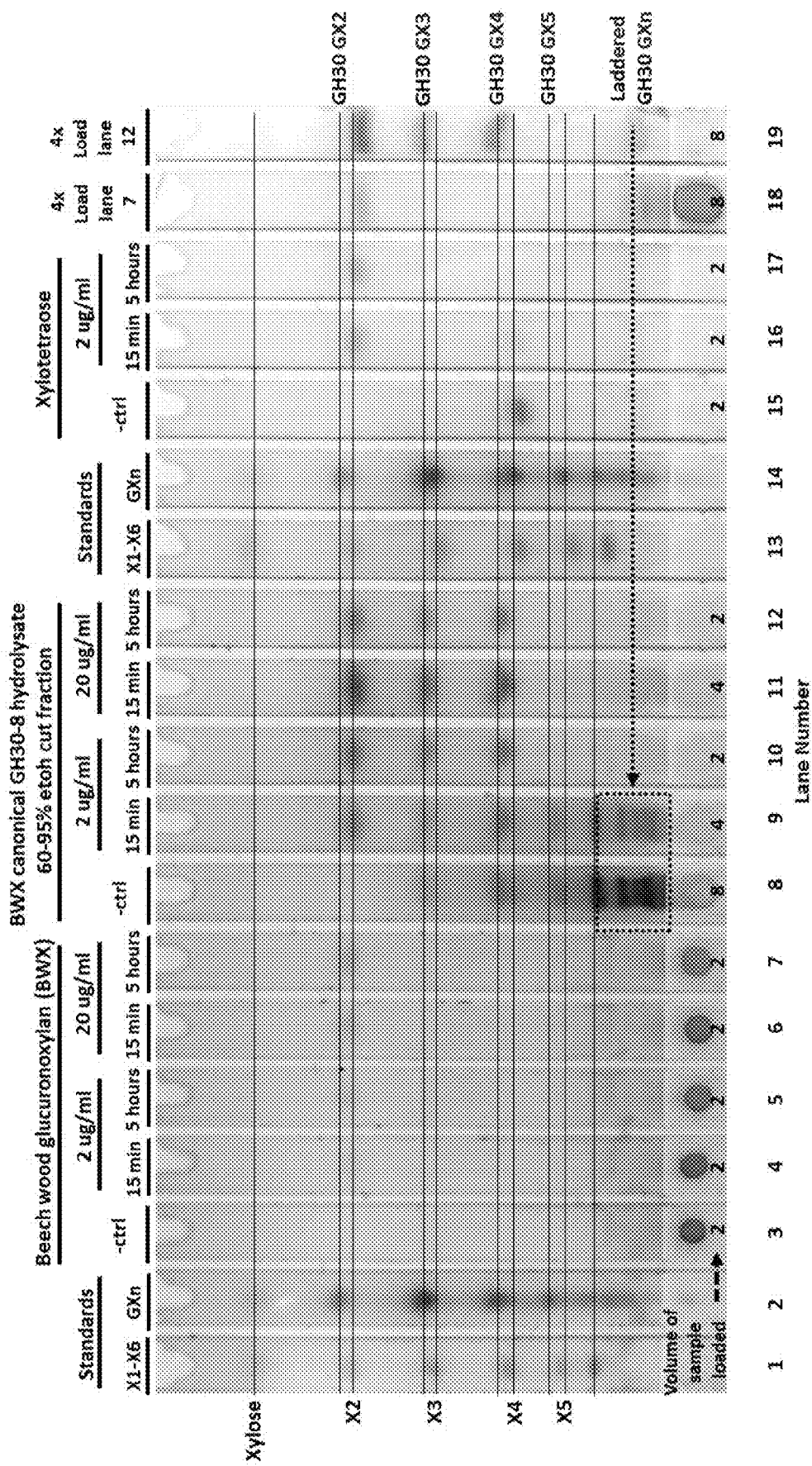
FIG. 8 shows TLC results that demonstrate that HcXbh30A does not exhibit secondary enzyme functions. Hydrolysis reactions of natural substrates were performed. Each reaction contained an amount of HcXbh30A (2 ug/ml) that should completely convert approximately 5 mM xylotetraose to xylobiose in 15 minutes at 70° C. Additionally, reactions were performed with 10× excess enzyme and 10× excess enzyme/20× reaction time to visualize any potential secondary products. The overload lanes (#18 & 19) reveal that xylobiose is the only product released from polymeric glucuronoxylan and that hydrolysis of aldouronates resulting from a GH30-8 limit hydrolysis (as exemplified by a canonical GH30-8, 60-95% ethanol cut fraction) is converted completely to xylobiose and the two expected aldouronic acids.

Results:

Using thin layer chromatography, we confirmed that HcXbh30A has xylobiohydrolase activity and that this activity is specific. We showed that HcXbh30A specifically releases xylobiose from both the glucuronoxylan beech xylan and the model xylooligosaccharides xylohexaose (FIG. 7). Additionally, we determined that HcXbh30A is not able to act as a cellobiohydrolase (FIG. 7), indicating that the C6 position of glucose is not accommodated in the HcXbh30A substrate-binding cleft. Finally, hydrolysis reactions performed with excess enzyme and extended reactions times indicated that HcXbh30A does not possess secondary enzyme functions (FIG. 8 and FIG. 9), demonstrating the specificity of this enzyme's activity.

Figure 3:
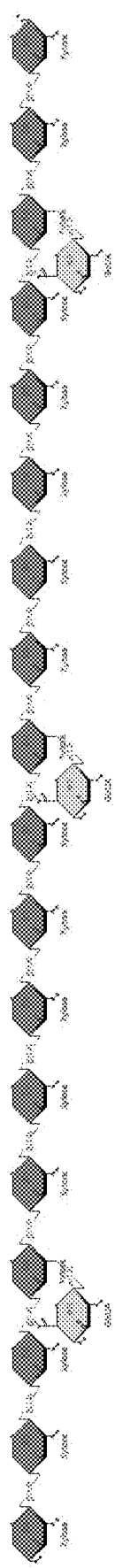
FIG. 3 shows a schematic of glycoside hydrolase family 30 subfamily 8 (GH30-8) glucuronoxylan xylanohydrolase hydrolysis sites in model hardwood glucuronoxylan.
Figure 5:
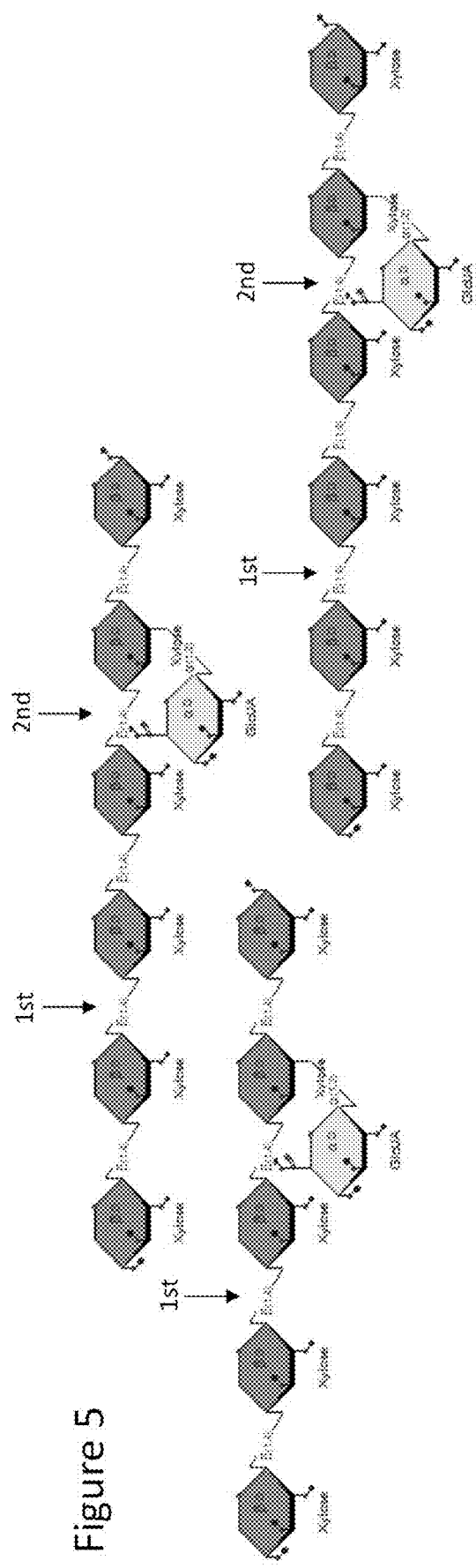
FIG. 5 shows a schematic of HcXbh30A hydrolysis sites in an aldouronate mixture generated by glucuronoxylan xylanohydrolase.
Figure 11:
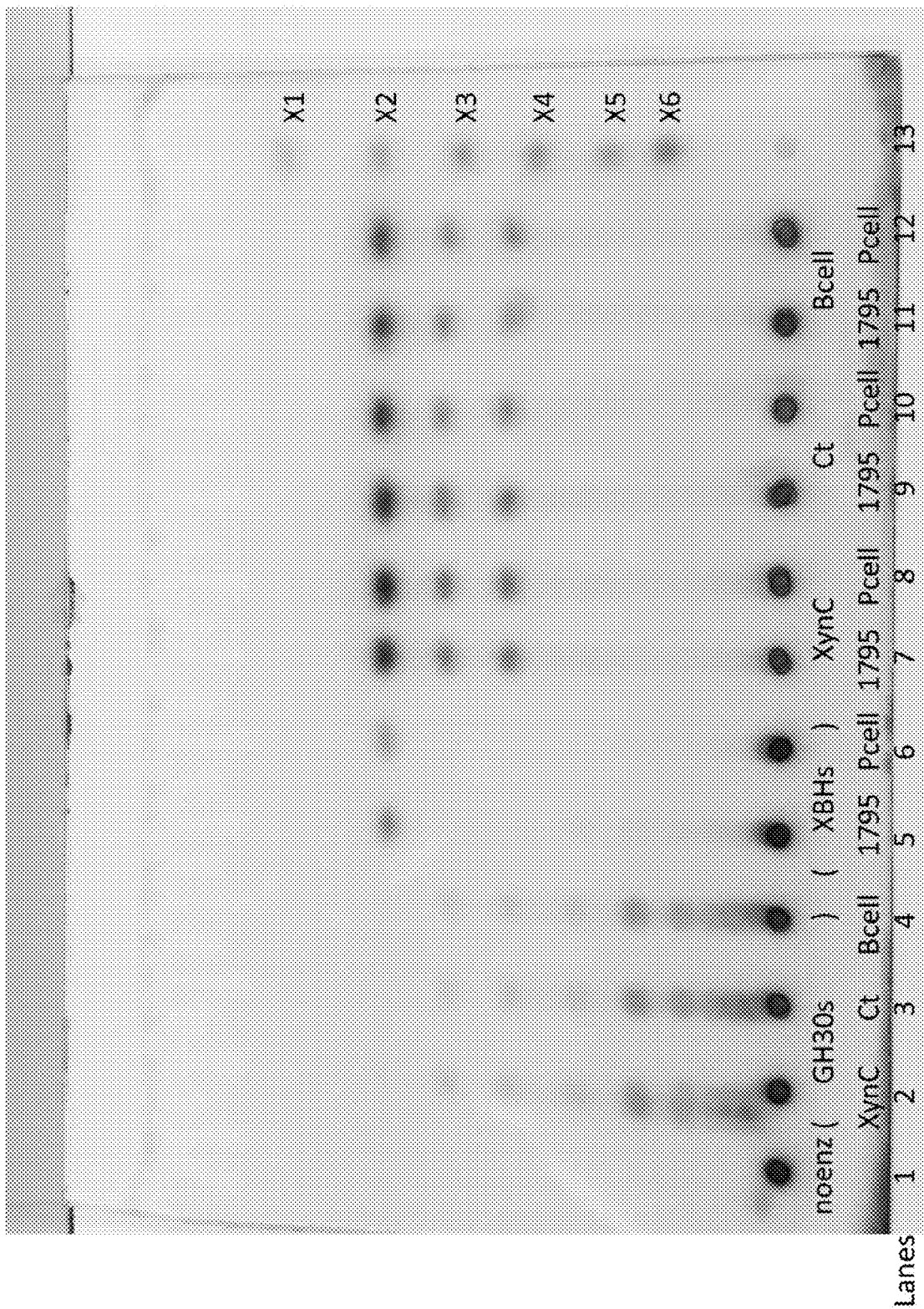
FIG. 11 shows TLC results following hydrolysis with three canonical GH30-8 endoxylanases, *Bacteroides cellulosilyticus* (NCBI Reference Sequence: WP 029428491.1; SEQ ID NO:19) [Bcell], *Bacillus subtilis* (UniProt: Q45070; SEQ ID NO:15) [XynC], *Clostridium thermocellum* (UniProt: A3DJS9; SEQ ID NO:14) [Ct], were shown to process the model beechwood glucuronoxylan as expected (lanes 2-4). Each of these GH30-8 glucuronoxylan hydrolysates were then subjected to the xylobiohydrolases *Hungateiclostridium clariflavum* (referred to herein as HcXbh30A; UniProt: G8LU16; SEQ ID NO:1) and *Pseudobacteroides cellulosolvens* (UniProt: A0A0L6JSW0; SEQ ID NO:2; Pcell) (lanes 7-12) to show that diverse canonical functioning GH30-8 glucuronoxylan xylanohydrolases work together as expected with the two tested GH30 xylobiohydrolases.

The Two-Enzyme System:

Enzymatic digestion of glucuronoxylan with a canonical glucuronoxylan xylanohydrolase-1,4-endoxylanase (e.g., GH30-8) requires the specific recognition of a glucuronate (GA) xylan chain decoration (FIG. 3) and yields a mixed population of aldouronates (i.e., xylooligosaccharides that contain at least a single GA) that are specifically GA substituted on the penultimate xylose from the reducing terminus. This population includes aldouronates spanning a broad size range (e.g., as small as aldotriuronic acid) and that have even and odd xylose subunits extending from the GA substitutions towards the non-reducing end (FIG. 4). The size distribution of the population is dictated by the GA substitution frequency and character (i.e., random vs periodic) of the exacted xylan that was processed. Treatment of this population with the xylobiohydrolase Clocl_1795 (or a derivative thereof) cleaves xylobiose from the non-reducing terminus of the aldouronates (FIG. 5). This hydrolysis reactions generates xylobiose and either aldotriuronic acid or aldotetrauronic acid (FIG. 6), depending on the even/odd length of the xylose chain extending towards the non-reducing terminus from the GA substitution and owing to the reducing terminus specificity of the GA-dependent hydrolysis providing a defined penultimate reducing end GA substitution. The difference in charge between these sugars can then be used to separate neutral xylobiose from the acidic aldouronates. The ability of this two-enzyme to produce the desired products is demonstrated in FIG. 11. Notably, both enzymes used in this method are functional between pH 2.5 and 9.0 and within the temperature range of 15-90° C.

Although specific embodiments are described above, it will be apparent to those of ordinary skill that a number of variations can be made within the scope of the disclosure. It should be understood, therefore, that the specific methods, compositions, and kits described above are only exemplary and do not limit the scope of the invention, and that various modifications could be made by those skilled in the art. To apprise the public of the scope of this invention, the following claims shall be referred to.

REFERENCES

Aachary, A. A., and Prapulla, S. G. (2011). Xylooligosaccharides (XOS) as an emerging prebiotic: microbial synthesis, utilization, structural characterization, bioactive properties, and applications. *Comprehensive Reviews in Food Science and Food Safety* 10(1), 2-16.

Anderson, V. R., and Perry, C. M. (2006). Pentosan polysulfate. *Drugs* 66(6), 821-835.

Artzi, L., Morag, E., Barak, Y., Lamed, R., and Bayer, E. A. (2015). *Clostridium clariflavum*: key cellulosome players are revealed by proteomic analysis. *MBio* 6(3), e00411-00415.

Bounias, M. (1980). N-(1-Naphthyl) ethylenediamine dihydrochloride as a new reagent for nanomole quantification of sugars on thin-layer plates by a mathematical calibration process. *Anal. Biochem.* 106(2), 291-295.

Broekaert, W. F., Courtin, C. M., Verbeke, K., Van de Wiele, T., Verstraete, W., and Delcour, J. A. (2011). Prebiotic and other health-related effects of cereal-derived arabinoxylans, arabinoxylan-oligosaccharides, and xylooligosaccharides. *Critical reviews in food science and nutrition* 51(2), 178-194.

Charalampopoulos, D., and Rastall, R. A. (2012). Prebiotics in foods. *Current opinion in biotechnology* 23(2), 187-191.

Chen, H. H., Chen, Y. K., Chang, H. C., and Lin, S. Y. (2012). Immunomodulatory effects of xylooligosaccharides. *Food Science and Technology Research* 18(2), 195-199.

Chung, Y.-C., Hsu, C.-K., Ko, C.-Y., and Chan, Y.-C. (2007). Dietary intake of xylooligosaccharides improves the intestinal microbiota, fecal moisture, and pH value in the elderly. *Nutrition Research* 27(12), 756-761.

Crittenden, R. a., and Playne, M. J. (1996). Production, properties and applications of food-grade oligosaccharides. *Trends in food science & technology* 7(11), 353-361.

da Silva, A. E., Marcelino, H. R., Gomes, M. C. S., Oliveira, E. E., Nagashima Jr, T., and Egito, E.S.T. (2012). *Xylan, a promising hemicellulose for pharmaceutical use.*

Daus, S., Petzold-Welcke, K., Kötteritzsch, M., Baumgaertel, A., Schubert, U. S., and Heinze, T. (2011). Homogeneous sulfation of xylan from different sources. *Macromolecular Materials and Engineering* 296(6), 551-561.

Ebringerova, A., and Hromadkova, Z. (1999). Xylans of industrial and biomedical importance. *Biotechnology & genetic engineering reviews* 16, 325-346.

Ebringerová, A., Kardošová, A., Hromádková, Z., Malovíková, A., and Hříbalová, V. (2002). Immunomodulatory activity of acidic xylans in relation to their structural and molecular properties. *International journal of biological macromolecules* 30(1), 1-6.

Escalante, A., Gonsalves, A., Bodin, A., Stepan, A., Sandström, C., Toriz, G., et al. (2012). Flexible oxygen barrier films from spruce xylan. *Carbohydrate Polymers* 87(4), 2381-2387.

Felsenstein J. (1985). Confidence limits on phylogenies: An approach using the bootstrap. Evolution 39:783-791.

Femia, A. P., Salvadori, M., Broekaert, W. F., Francois, I. E., Delcour, J. A., Courtin, C. M., et al. (2010). Arabinoxylan-oligosaccharides (AXOS) reduce preneoplastic lesions in the colon of rats treated with 1, 2-dimethylhydrazine (DMH). *European journal of nutrition* 49(2), 127-132.

Finegold, S. M., Li, Z., Summanen, P. H., Downes, J., Thames, G., Corbett, K., et al. (2014). Xylooligosaccharide increases bifidobacteria but not lactobacilli in human gut microbiota. *Food & Function* 5(3), 436-445.

Geraylou, Z., Souffreau, C., Rurangwa, E., D'hondt, S., Callewaert, L., Courtin, C. M., et al. (2012). Effects of arabinoxylan-oligosaccharides (AXOS) on juvenile Siberian sturgeon (Acipenser baerii) performance, immune responses and gastrointestinal microbial community. *Fish & shellfish immunology* 33(4), 718-724.

Gibson, G. R., Hutkins, R., Sanders, M. E., Prescott, S. L., Reimer, R. A., Salminen, S. J., et al. (2017). Expert consensus document: The International Scientific Association for Probiotics and Prebiotics (ISAPP) consensus statement on the definition and scope of prebiotics. *Nature Reviews Gastroenterology & Amp; Hepatology* 14, 491. doi: 10.1038/nrgastro.2017.75.

Gibson, G. R., and Roberfroid, M. B. (1995). Dietary modulation of the human colonic microbiota: introducing the concept of prebiotics. *The Journal of nutrition* 125(6), 1401-1412.

Goodrich, L. R., and Nixon, A. J. (2006). Medical treatment of osteoarthritis in the horse—a review. *The Veterinary Journal* 171(1), 51-69.

Hsu, C.-K., Liao, J.-W., Chung, Y.-C., Hsieh, C.-P., and Chan, Y.-C. (2004). Xylooligosaccharides and fructooligosaccharides affect the intestinal microbiota and precancerous colonic lesion development in rats. *The Journal of nutrition* 134(6), 1523-1528.

Jones D. T., Taylor W. R., and Thornton J. M. (1992). The rapid generation of mutation data matrices from protein sequences. Computer Applications in the Biosciences 8: 275-282.

Kamdem, D. P., Shen, Z., Nabinejad, O., and Shu, Z. (2019). Development of biodegradable composite chitosan-based films incorporated with xylan and carvacrol for food packaging application. *Food Packaging and Shelf Life* 21, 100344.

Kaprelyants, L., Zhurlova, O., Shpyrko, T., and Pozhitkova, L. (2017). Xylooligosaccharides from agricultural by-products: characterisation, production and physiological effects. *Food Science and Technology* 11(3).

Kardošová, A., Ebringerová, A., Alföldi, J., Nosál'ová, G., Matáková, T., and Hříbalová, V. (2004). Structural features and biological activity of an acidic polysaccharide complex from *Mahonia aquifolium* (Pursh) Nutt. *Carbohydrate polymers* 57(2), 165-176.

Khat-udomkiri, N., Toejing, P., Sirilun, S., Chaiyasut, C., and Lailerd, N. (2020). Antihyperglycemic effect of rice husk derived xylooligosaccharides in high-fat diet and low-dose streptozotocin-induced type 2 diabetic rat model. *Food science & nutrition* 8(1), 428-444.

Kobayashi, Y., Wakasugi, E., Ohbuchi, T., Yokoyama, M., Yasui, R., Kuwahata, M., et al. (2011). Acidic Xylooligosaccharide promotes recovery from iron deficiency anemia by enhancing serum iron level in rats. *Biomedical Research* 22(4), 417-423.

Kumar S., Stecher G., Li M., Knyaz C., and Tamura K. (2018). MEGA X: Molecular Evolutionary Genetics Analysis across computing platforms. Molecular Biology and Evolution 35:1547-1549.

Kuzmenko, V., Hagg, D., Toriz, G., and Gatenholm, P. (2014). In situ forming spruce xylan-based hydrogel for cell immobilization. *Carbohydrate polymers* 102, 862-868.

Lim, S. H., Kim, Y., Yun, K. N., Kim, J. Y., Jang, J.-H., Han, M.-J., et al. (2016). Plant-based foods containing cell wall polysaccharides rich in specific active monosaccharides protect against myocardial injury in rat myocardial infarction models. *Scientific reports* 6, 38728.

Mäkeläinen, H., Forssten, S., Saarinen, M., Stowell, J., Rautonen, N., and Ouwehand, A. (2009). Xylo-oligosaccharides enhance the growth of bifidobacteria and *Bifidobacterium lactis* in a simulated colon model. *Beneficial Microbes* 1(1), 81-91.

Mano, M. C. R., Neri-Numa, I. A., da Silva, J. B., Paulino, B. N., Pessoa, M. G., and Pastore, G. M. (2017). Oligosaccharide biotechnology: an approach of prebiotic revolution on the industry. *Applied Microbiology and Biotechnology*, 1-21.

Mathews, S. L., Pawlak, J., and Grunden, A. M. (2015). Bacterial biodegradation and bioconversion of industrial lignocellulosic streams. *Applied Microbiology and Biotechnology*, 1-16.

McIlwraith, C. W., Frisbie, D. D., and Kawcak, C. E. (2012). Evaluation of intramuscularly administered sodium pentosan polysulfate for treatment of experimentally induced osteoarthritis in horses. *American journal of veterinary research* 73(5), 628-633.

Munteanu, S. E., Ilic, M. Z., and Handley, C. J. (2000). Calcium pentosan polysulfate inhibits the catabolism of aggrecan in articular cartilage explant cultures. *Arthritis & Rheumatism: Official Journal of the American College of Rheumatology* 43(10), 2211-2218.

Nishitani, K., and Nevins, D. (1991). Glucuronoxylan xylanohydrolase. A unique xylanase with the requirement for appendant glucuronosyl units. *Journal of Biological Chemistry* 266(10), 6539-6543.

Oehme, D., Ghosh, P., Shimmon, S., Wu, J., McDonald, C., Troupis, J. M., et al. (2014). Mesenchymal progenitor cells combined with pentosan polysulfate mediating disc regeneration at the time of microdiscectomy: a preliminary study in an ovine model. *Journal of Neurosurgery: Spine* 20(6), 657-669.

Ohbuchi, T., Sakaino, M., Takahashi, T., Azumi, N., Ishikawa, K., Kawazoe, S., et al. (2010). *Oral administration of acidic xylooligosaccharides prevents the development of atopic dermatitis-like skin lesions in NC/Nga mice. Journal of nutritional science and vitaminology* 56(1), 54-59.

Rhee, M. S., Wei, L., Sawhney, N., Rice, J. D., St John, F. J., Hurlbert, J. C., et al. (2014). Engineering the xylan utilization system in *Bacillus subtilis* for production of acidic xylooligosaccharides. *Applied and environmental microbiology* 80(3), 917-927.

Saha, B. C. (2003). Hemicellulose bioconversion. *J. Ind. Microbiol. Biotechnol.* 30(5), 279-291.

Saitou N. and Nei M. (1987). The neighbor-joining method: A new method for reconstructing phylogenetic trees. Molecular Biology and Evolution 4:406-425.

Schuchman, E. H., Ge, Y., Lai, A., Borisov, Y., Faillace, M., Eliyahu, E., et al. (2013). Pentosan Polysulfate: A Novel Therapy for the Mucopolysaccharidoses. *PLOS One* 8(1), e54459.

St John, F. J., Dietrich, D., Crooks, C., Balogun, P., de Serrano, V., Pozharski, E., et al. (2018). A plasmid borne, functionally novel glycoside hydrolase family 30 subfamily 8 endoxylanase from solventogenic *Clostridium*. *Biochemical Journal* 475(9), 1533-1551.

St John, F. J., Dietrich, D., Crooks, C., Pozharski, E., Gonzalez, J. M., Bales, E., Smith, K. & Hurlbert, J. C. (2014) A novel member of glycoside hydrolase family 30 subfamily 8 with altered substrate specificity, Acta Crystallogr D Biol Crystallogr. 70, 2950-2958.

St John, F. J., Hurlbert, J. C., Rice, J. D., Preston, J. F., and Pozharski, E. (2011). Ligand bound structures of a glycosyl hydrolase family 30 glucuronoxylan xylanohydrolase. *J Mol. Biol.* 407(1), 92-109.

St John, F. J., J. M. Gonzalez and E. Pozharski (2010). "Consolidation of glycosyl hydrolase family 30: a dual domain 4/7 hydrolase family consisting of two structurally distinct groups." *FEBS Lett.* 584(21): 4435-4441.

St John, F. J., Rice, J. D., and Preston, J. F. (2006a). Characterization of XynC from *Bacillus subtilis* subsp. *subtilis* strain 168 and analysis of its role in depolymerization of glucuronoxylan. *J Bacteriol.* 188(24), 8617-8626.

St John, F. J., Rice, J. D., and Preston, J. F. (2006b). *Paenibacillus* sp. strain JDR-2 and XynA1: a novel system for methylglucuronoxylan utilization. *Applied and environmental microbiology* 72(2), 1496-1506.

Studier, F. W. (2005). Protein production by auto-induction in high-density shaking cultures. *Protein expression and purification* 41(1), 207-234.

Ünlü C. H., Günister, E., and Atici, O. (2009). Synthesis and characterization of NaMt biocomposites with corn cob xylan in aqueous media. *Carbohydrate Polymers* 76(4), 585-592.

Urbániková, L., Vršanská, M., Morkeberg Krogh, K. B., Hoff, T., and Biely, P. (2011). Structural basis for substrate recognition by Envinia chrysanthemi GH30 glucuronoxylanase. *FEBS 1* 278, 2105.

Vazquez, M., Alonso, J., Dominguez, H., and Parajo, J. (2000). Xylooligosaccharides: manufacture and applications. *Trends in Food Science & Technology* 11(11), 387-393.

Vršanská, M., Kolenová, K., Puchart, V., and Biely, P. (2007). Mode of action of glycoside hydrolase family 5 glucuronoxylan xylanohydrolase from *Erwinia chrysanthemi*. *Febs J.* 274(7), 1666-1677.

Yang, J., Summanen, P. H., Henning, S. M., Hsu, M., Lam, H. M., Huang, J., et al. (2015). Xylooligosaccharide supplementation alters gut bacteria in both healthy and prediabetic adults: a pilot study. *Frontiers in physiology* 6, 216.

What is claimed:

1. A composition configured to produce xylobiose, $2^2$-(4-O-methyl-α-D-glucuronosyl)-xylobiose [aldotriuronic acid], and $2^2$-(4-O-methyl-α-D-glucuronosyl)-xylotriose [aldotetrauronic acid], the composition comprising:
   a) an isolated appendage dependent endoxylanase that is a canonical glycoside hydrolase family 30 subfamily 8 (GH30-8) enzyme having at least 90% identity to a sequence selected from the group consisting of SEQ ID NO: 14, 18, and 19; and
   b) an isolated xylobiohydrolase comprising an amino acid sequence with at least 90% identity to a sequence selected from the group consisting of SEQ ID NO: 1, 9, and 10 or a portion thereof with xylobiohydrolase activity.

2. The composition of claim 1, further comprising:
   c) a lignocellulosic biomass material, an enriched xylan fraction thereof, or an extracted, purified xylan material.

3. The composition of claim 2, wherein the lignocellulosic biomass material is pulped.

4. The composition of claim 2, wherein the lignocellulosic biomass material is obtained from hardwood, softwood, or grass.

5. The composition of claim 2, wherein the lignocellulosic biomass material comprises glucuronoxylans or glucuronoarabinoxylans.

6. The composition of claim 1 further comprising an additional enzyme that is different than the isolated appendage dependent endoxylanase.

7. The composition of claim 6, wherein the additional enzyme is selected from arabinofuranosidases, arabinoxylanases, β-xylosidases, and α-glucuronidases.

8. A method for producing xylobiose, the method comprising contacting a lignocellulosic biomass material, an enriched xylan fraction thereof, or an extracted, purified xylan material with:
   a) an isolated appendage dependent endoxylanase that is a canonical glycoside hydrolase family 30 subfamily 8 (GH30-8) enzyme having at least 90% identity to a sequence selected from the group consisting of SEQ ID NO: 14, 18, and 19; and
   b) an isolated xylobiohydrolase comprising an amino acid sequence with at least 90% identity to a sequence selected from the group consisting of SEQ ID NO: 1, 9, and 10 or a portion thereof with xylobiohydrolase activity;
   thereby producing a product mixture comprising xylobiose, $2^2$-(4-O-methyl-α-D-glucuronosyl)-xylobiose [aldotriuronic acid], and $2^2$-(4-O-methyl-α-D-glucuronosyl)-xylotriose [aldotetrauronic acid].

9. The method of claim 8 further comprising:
   c) isolating xylobiose from the product mixture.

10. The method of claim 8, wherein the lignocellulosic biomass material, the enriched xylan fraction thereof, or the extracted, purified xylan material is contacted with the isolated appendage dependent endoxylanase before it is contacted with the xylobiohydrolase.

11. The method of claim 8 further comprising additionally contacting the lignocellulosic biomass material, the enriched xylan fraction thereof, or the extracted, purified xylan material with an arabinofuranosidase, or a β-xylosidase, or an α-glucuronidase, or an arabinoxylanase, thereby yielding alternative populations of alpha-1,3-linked arabinofuranose substituted xylooligosaccharides or aldouronates.

12. The method of claim 8, wherein the lignocellulosic biomass material is obtained from hardwood, softwood, or grass.

13. The method of claim 8, wherein the lignocellulosic biomass material comprises glucuronoxylans.

14. The method of claim 13 further comprising extracting the glucuronoxylans from hardwood using alkaline extraction.

15. The method of claim 8, wherein the lignocellulosic biomass material comprises glucuronoarabinoxylans or arabinoglucuronoxylans.

16. The method of claim 15 further comprising pretreating the glucuronoarabinoxylan to remove arabinose.

17. The method of claim 8, wherein the product mixture further comprises arabinofuranose-substituted aldouronates.

18. The composition of claim 1, wherein the isolated appendage dependent endoxylanase and the isolated xylobiohydrolase are each provided as nucleic acid constructs that encode the respective enzymes.

19. The method of claim 8, wherein the isolated appendage dependent endoxylanase and the isolated xylobiohydrolase are each provided as nucleic acid constructs that encode the respective enzymes.

* * * * *